(12) United States Patent
Malackowski et al.

(10) Patent No.: US 7,422,582 B2
(45) Date of Patent: Sep. 9, 2008

(54) CONTROL CONSOLE TO WHICH POWERED SURGICAL HANDPIECES ARE CONNECTED, THE CONSOLE CONFIGURED TO SIMULTANEOUSLY ENERGIZE MORE THAN ONE AND LESS THAN ALL OF THE HANDPIECES

(75) Inventors: Don Malackowski, Schoolcraft, MI (US); Michael D. Dozeman, Kalamazoo, MI (US); Paul M. Hoekstra, Kalamazoo, MI (US); Michael R. Wildgen, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 515 days.

(21) Appl. No.: 10/955,381

(22) Filed: Sep. 30, 2004

(65) Prior Publication Data

US 2006/0074405 A1    Apr. 6, 2006

Related U.S. Application Data

(60) Provisional application No. 60/614,089, filed on Sep. 29, 2004.

(51) Int. Cl.
A61B 17/00 (2006.01)
(52) U.S. Cl. ............................ 606/1; 606/32
(58) Field of Classification Search ............ 606/1, 606/32
See application file for complete search history.

(56) References Cited

U.S. PATENT DOCUMENTS

| 4,162,435 | A | 7/1979 | Wright | 318/138 |
|---|---|---|---|---|
| 4,876,491 | A | 10/1989 | Squires et al. | 318/138 |
| 5,117,165 | A | 5/1992 | Cassat et al. | 318/254 |
| 5,609,560 | A | 3/1997 | Ichikawa | |
| 6,017,354 | A | 1/2000 | Culp et al. | 606/170 |
| 6,037,724 | A | 3/2000 | Buss | |
| 2001/0029315 | A1 | 10/2001 | Sakurai | |
| 2002/0183585 | A1 | 12/2002 | Willems | |
| 2003/0093103 | A1 | 5/2003 | Malackowski et al. | |
| 2003/0144649 | A1 | 7/2003 | Ghodoussi | |
| 2004/0158237 | A1* | 8/2004 | Abboud et al. | 606/21 |

FOREIGN PATENT DOCUMENTS

WO    WO 03/013372 A    2/2003

OTHER PUBLICATIONS

Fairchild Semiconductor, App. Brief 42020 The Smart Start Technique For BLDC Motors, Oct. 2000.
ConMed PowerPro System Material from www.conmed.com/products-powerprocon.php Sep. 2004.
ConMed/Linvatec, PowerPro Advantage Console Advertisement www.conmed.com, Sep. 2004.
PCT App. No. PCT/US2005/034800, Internation Search Report, Jun. 29, 2006.
PCT App. No. PCT/US2005/034800, Written Opinion of the International Search Authority, Jun. 29, 2006.

* cited by examiner

*Primary Examiner*—Roy D. Gibson
*Assistant Examiner*—Pete Vrettakos

(57) ABSTRACT

A surgical tool system including plural powered surgical handpieces. The handpieces are removably connected to a single control console. The control console has a power supply. A controller internal to the control console simultaneously supplies power to the plural handpieces. In the event the handpieces collectively draw more power than the power supply can provide, the control console temporarily stops the application of power to one of the handpieces.

6 Claims, 33 Drawing Sheets

126

| | |
|---|---|
| KNEE REPLACEMENT | 128 |
| ACL | 128 |
| ANKLE TRAUMA | 128 |
| TIBIA TRAUMA | 128 |

| | |
|---|---|
| DR. SMITH KNEE REPLACEMENT | 132 |
| DR. SMITH ACL | 132 |
| CHEST TRAUMA | 132 |
| DR. JONES KNEE REPLACEMENT | 132 |

| | |
|---|---|
| PEDAL 1 ASSIGNMENT | 152 |
| PEDAL 2 ASSIGNMENT | 152 |
| PEDAL 3 ASSIGNMENT | 152 |
| PEDAL 4 ASSIGNMENT | 152 |
| PEDAL 5 ASSIGNMENT | 152 |

FIG. 10

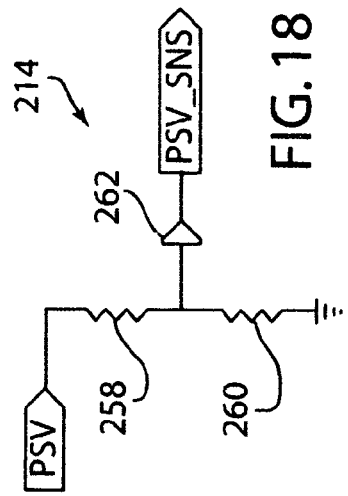
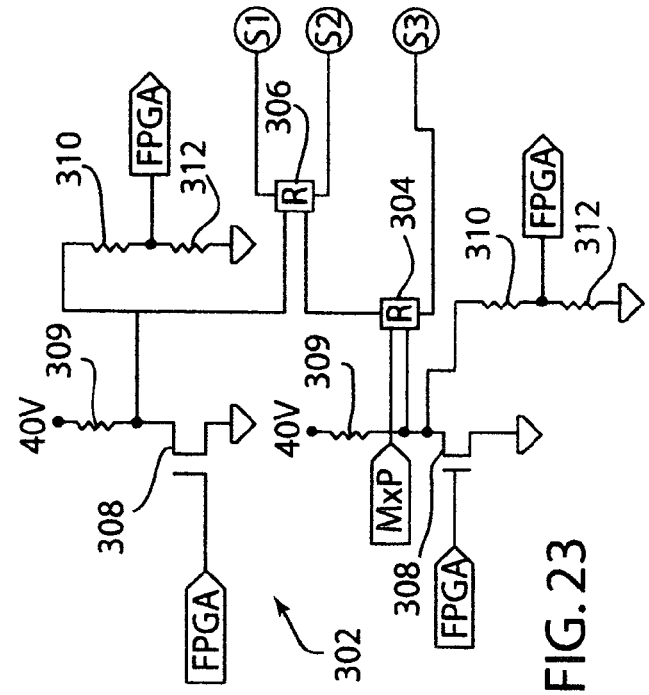
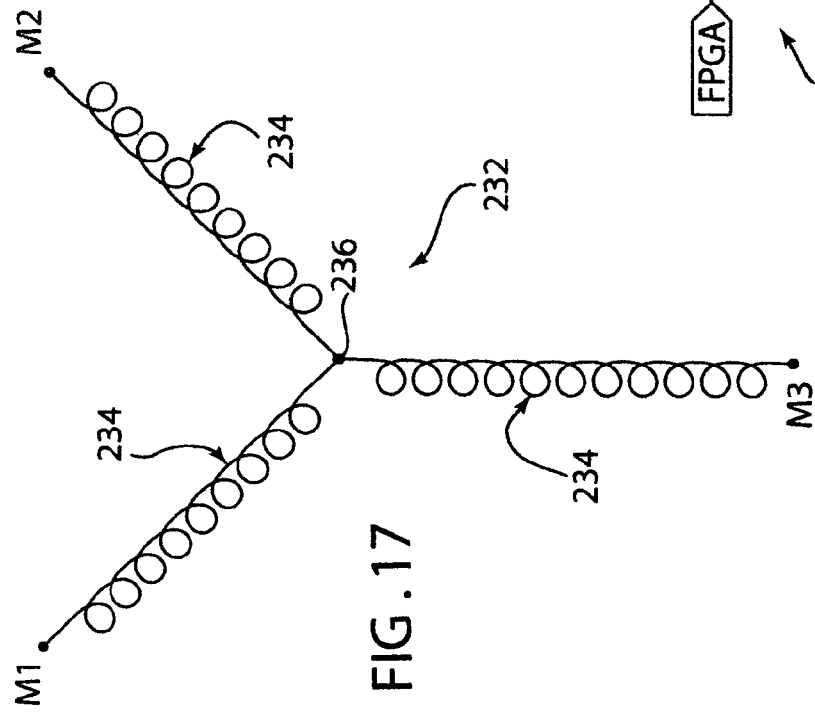

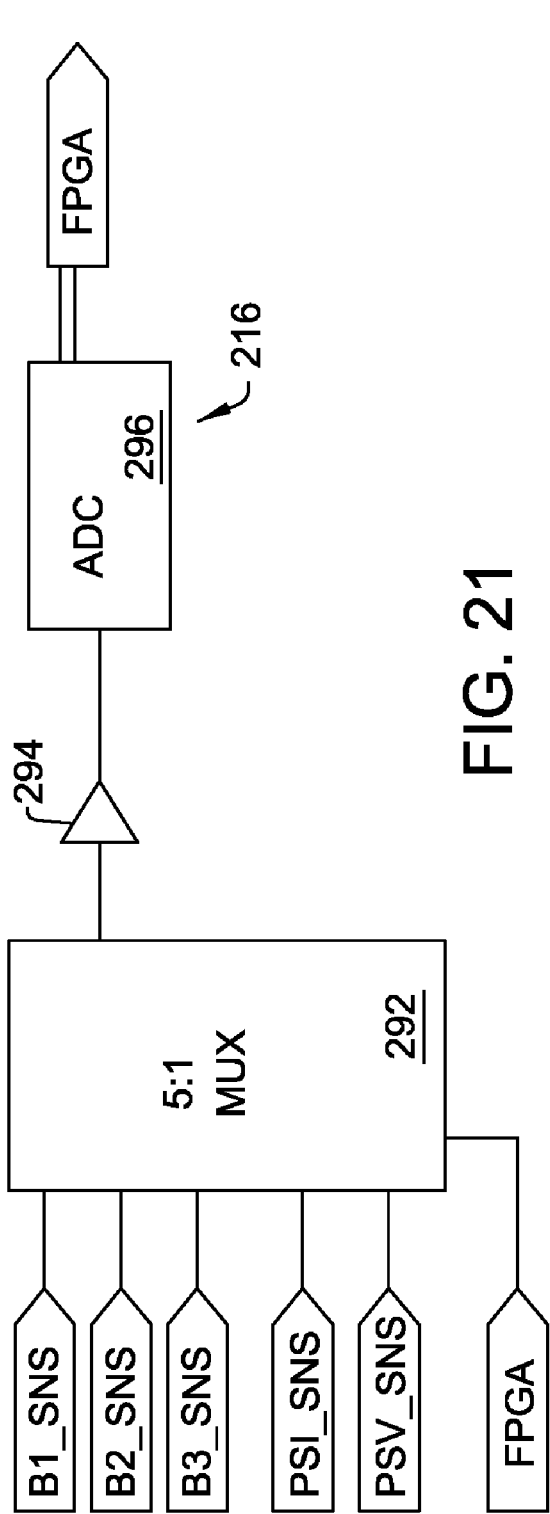
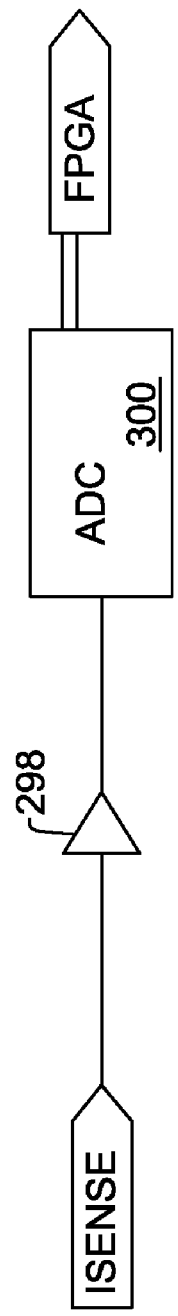
FIG. 21
FIG. 22

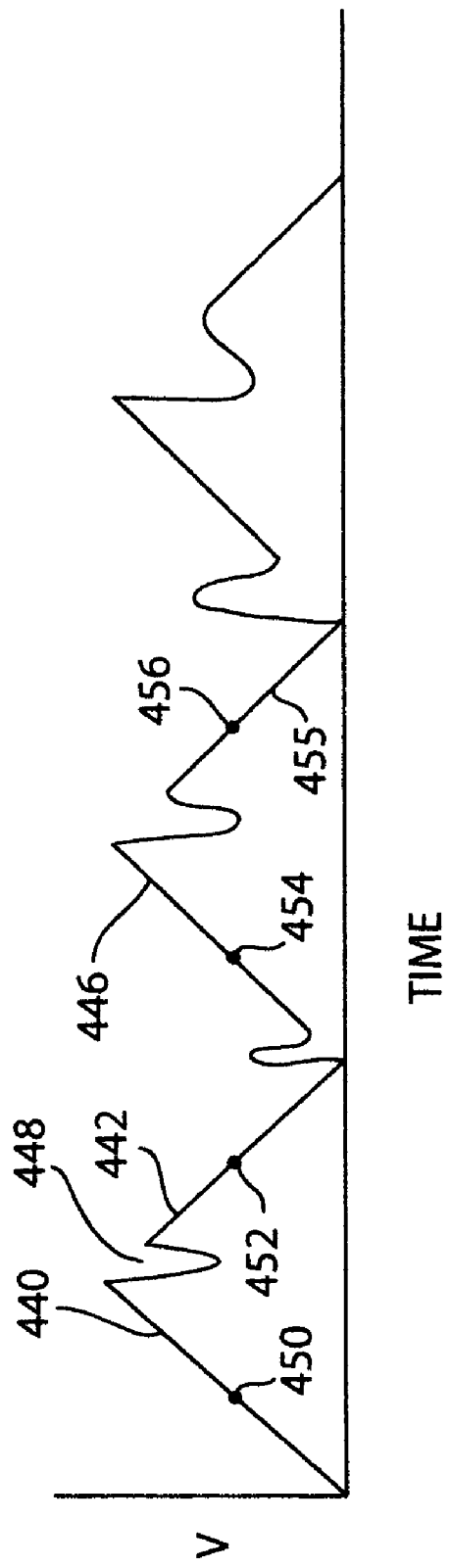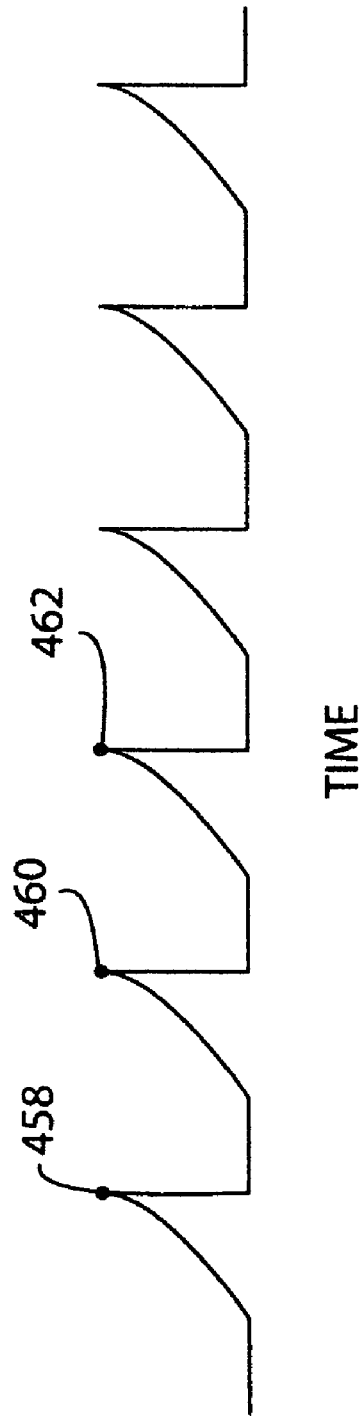

CONTROL CONSOLE TO WHICH POWERED SURGICAL HANDPIECES ARE CONNECTED, THE CONSOLE CONFIGURED TO SIMULTANEOUSLY ENERGIZE MORE THAN ONE AND LESS THAN ALL OF THE HANDPIECES

RELATIONSHIP TO EARLIER FILED APPLICATION

This application claims priority under 35 U.S.C. Sec 119 from Provisional Application No. 60/614,089, having the same title as this application, filed Sep. 29, 2004 under Express Mail Label No. ER 5757 09335 US.

FIELD OF THE INVENTION

This invention is related generally to a system for powering surgical tools. More particularly, this invention is related to a system for simultaneously powering surgical tools that have different power requirements.

BACKGROUND OF THE INVENTION

In modern surgery, powered surgical tools are some of the most important instruments medical personnel have available to them for performing certain surgical procedures. Many surgical tools take the form of some type of motorized handpiece to which a cutting accessory like a drill bit, a bur or a saw blade are attached. These tools are used to selectively remove small sections of hard or soft tissue or to separate sections of tissue. The ability to use powered surgical tools on a patient has lessened the physical strain of physicians and other personnel when performing surgical procedures on a patient. Moreover, most surgical procedures can be performed more quickly and more accurately with powered surgical tools than with the manual equivalents that preceded them.

A typical powered surgical tool system, in addition to the handpiece, includes a control console and a cable that connects the handpiece to the console. The control console contains the electronic circuitry that converts the available line voltage into energization voltage suitable for powering the motor integral with the handpiece. Typically, the control console is connected to receive a signal from the hand or foot switch used to control the tool; based on that signal, the console sends appropriate energization signals to the handpiece so as to cause it to operate at the desired speed.

As the use of powered surgical tools has expanded, so has the development of different kinds of powered surgical tools that perform different surgical tasks. For example, a femoral reamer, used in hip replacement surgery is a relatively slow speed drill that operates at approximately 100 RPM, yet it draws a relatively high amount of power, approximately 400 Watts. Neurosurgery requires the use of a craniotome which is a very high powered drill that operates at approximately 75,000 RPM and that requires a medium amount of power, approximately 150 Watts. In ear, nose and throat surgery, micro drills are often employed. A typical micro drill rotates between approximately 10,000 and 40,000 RPM and requires only a relatively small amount of power, approximately 40 Watts.

As the number of different types of powered surgical tools have expanded, it has become necessary to provide each type of handpiece a mechanism for ensuring that it receives the appropriate energization signals. The conventional solution to this problem has been to provide each handpiece with its own power console. As can readily be understood, this solution is expensive in that it requires hospitals and other surgical facilities to keep a number of different consoles available, in the event a specific set of tools are required to perform a given surgical procedure. Moreover, in the event a number of different surgical tools are required in order to perform a given surgical procedure, it is necessary to provide the operating suite with the individual consoles required by the different handpieces. Having to provide these different consoles contributes to clutter in the operating suite.

An attempt to resolve this issue has been to design consoles that supply power to different handpieces. While these consoles have performed satisfactorily, they are not without their own disadvantages. Many of these consoles are arranged so that the medical personnel have to manually preset their internal electronics in order to ensure that they be provided the desired energization signals to the tools to which they are connected. Moreover, given the inevitable human error factor, time also needs to be spent to ensure that once configured for a new tool, a console is, in fact, properly configured. Requiring medical personnel to perform these tasks takes away from the time the personnel could be attending to the needs of the patient.

The Applicant's Assignee's U.S. Pat. No. 6,017,354, INTEGRATED SYSTEM FOR POWERED SURGICAL TOOLS, issued Jan. 25, 2000 the contents of which is explicitly incorporated herein by reference, appreciably eliminates the need to bring different control consoles into an operating room when surgical handpieces having different power requirements are used. In the disclosed system, each handpiece contains a NOVRAM. The NOVRAM stores data identifying the electrical power needs of the energy-producing component in the handpiece. The system also includes control console includes a processor and an energization circuit that for supplying energization signals applied to the handpiece. The types of the energization signals the energization circuit supplies to the handpiece vary as a function of command signals sent by the processor. Upon the connection of a handpiece to the control console, the data in the handpiece NOVRAM are read. These data are then used by the processor to regulate the output of energization signals by the energization circuit so that the appropriate energization signals are supplied to the handpiece.

Still another feature of the prior art system is that it is possible to simultaneously connect plural handpieces to the control console. The processor simultaneously stores the energization signal-describing data for each connected handpiece.

Thus, the prior art system, for many surgical procedures, essentially eliminated the need to provide an operating room with plural control consoles just because the handpieces being used had different power requirements. Moreover, the above system was further designed so that the console could be used to sequentially energize different handpieces without first having to remove the first and handpiece and then install the second handpiece.

Clearly, the prior art system provided a number of different cost and time efficiencies to the operating room. However, this system can, at a given instant, only supply power to a single handpiece. There are instances wherein for efficiency or necessity it is desirable to simultaneously actuate plural handpieces during a surgical procedure. For example, sometimes one surgeon will be harvesting tissue from one portion of a patient while a second surgeon is preparing another portion of the patient's body for insertion of the tissue. The present system is not able to simultaneously power the two separate surgical handpieces used to perform these separate procedures. If, in the interest of efficiency, there is an interest in performing these procedures simultaneously, two separate control consoles must be provided.

Moreover, many surgeons use footswitches to control their surgical handpieces and accessory instruments, for example, irrigation and suction pumps. It is a common practice to provide, on a single footswitch assembly, a number of different footswitches for controlling a number of different functions. For example, a single footswitch assembly may have individual footswitches for controlling the on/off state of the handpiece motor, the speed of the handpiece motor, the forward/reverse/oscillate direction of the handpiece motor and whether or not irrigation fluid is to be supplied.

Another limitation associated with known systems for driving motorized surgical handpieces concerns their ability to control the associated handpieces when the motors are operating at low RPMs. This problem is especially prevalent in systems employed to drive handpieces that include brushless, sensorless DC motors. The known systems operate by monitoring the back electromotive force voltage (BEMF signal) produced at the unenergized winding of the motor. A limitation associated with this control technique is that, when the motor is operating at a low RPM, the BEMF signal is often so low that it is difficult, if not impossible, to measure. Once this signal is undetectable, it can be no longer user to regular the commutation of the windings. Instead, brut force means are often used when the motor is started up in order to initially actuate the rotor. Also, this typical means that once a motor stalls as result of the motor reaching limit as the amount of torque that it can develop, the surgeon must totally deactivate, turn off, the motor before, the complementary control console can again apply a commutation signal to the windings. This results in the undesirable slowing of the surgical procedure.

SUMMARY OF THE INVENTION

This invention is related to a new and useful surgical tool system. The surgical tool system of this invention includes a control console. Internal to the control console is a motor controller capable of simultaneously energizing plural surgical handpieces. The control console also includes a display controller. The display controller functions as the main controller for the system. The display controller serves as the controller for the console. The display controller is capability of reading the data in the NOVRAMs in the handpieces connected to the console. Based on these data, additional data read by the console, externally generated commands and surgeon-entered commands, the main processor directs the motor controller to energize the handpieces.

BRIEF DESCRIPTION OF THE DRAWINGS

The invention is pointed out with particularity in the claims. The above and further features of the invention may be better understood by reference to the following description taken in conjunction with the accompanying drawings in which:

FIG. 7 depicts the records contained within an exemplary preference directory;

FIG. 8 is an example of the records contained within the active preference table;

FIG. 10 is a table illustrating the data fields within footswitch assignment table;

FIG. 17 is schematic representation of the stator windings of a handpiece motor;

FIG. 18 is a block and partial schematic diagram of the circuit used to monitor the power supply voltage;

FIG. 21 is a block diagram of the circuit used to convert a number of the monitored signals into digital signals;

FIG. 22 is a block diagram of the circuit used to convert the monitored current signal into a digital signal;

FIG. 23 is a block and partially schematic of one of the relay assemblies that for the motor multiplexer of the motor controller;

FIG. 34A is a graphic depiction of the BEMF signal over time and FIG. 34B depicts how, according the BEMF signal is measured according to this invention to determine motor rotor position.

DETAILED DESCRIPTION

Figure 1:
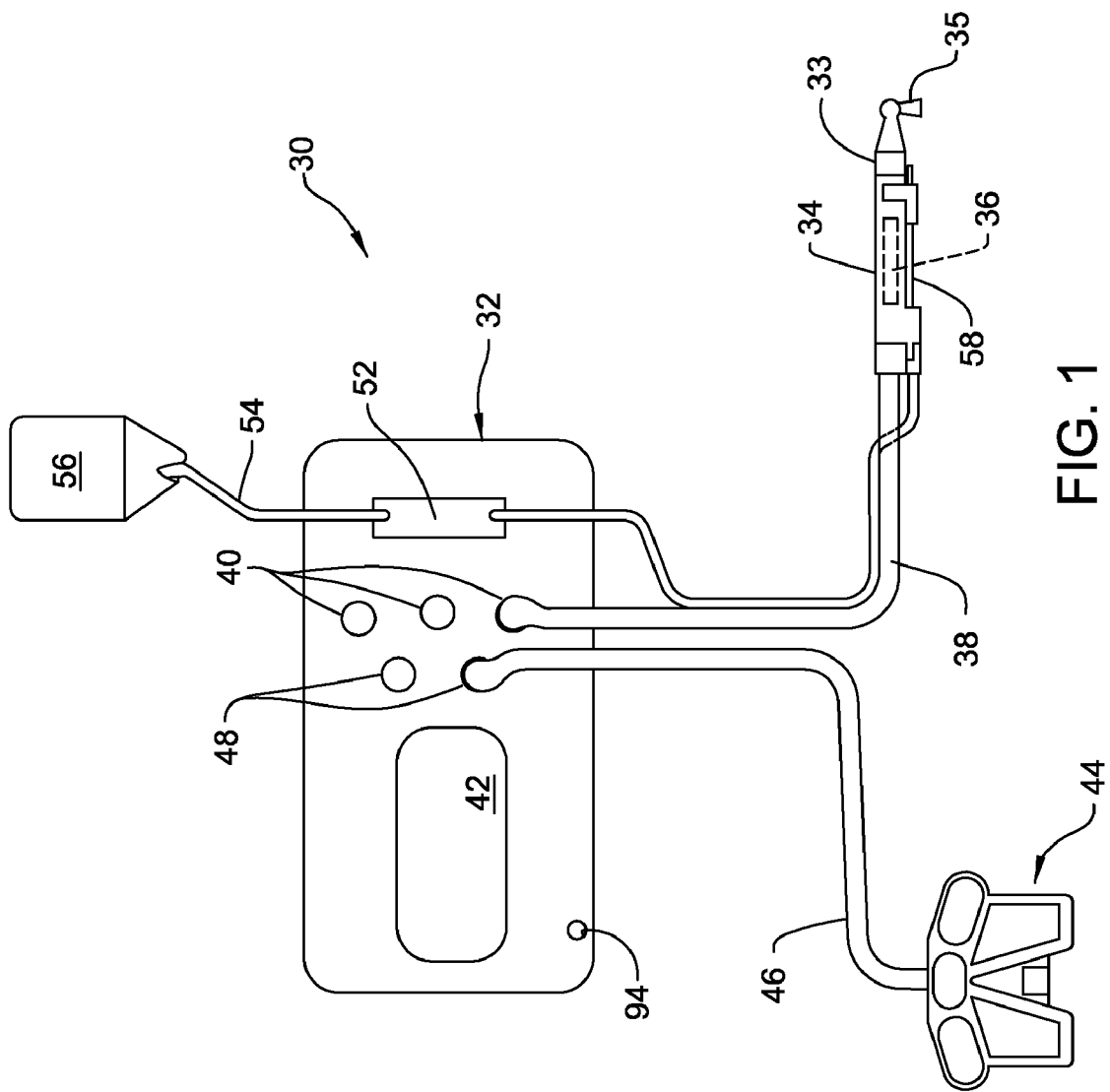
FIG. 1 depicts the basic components of the system of this invention.
Figure 2A:
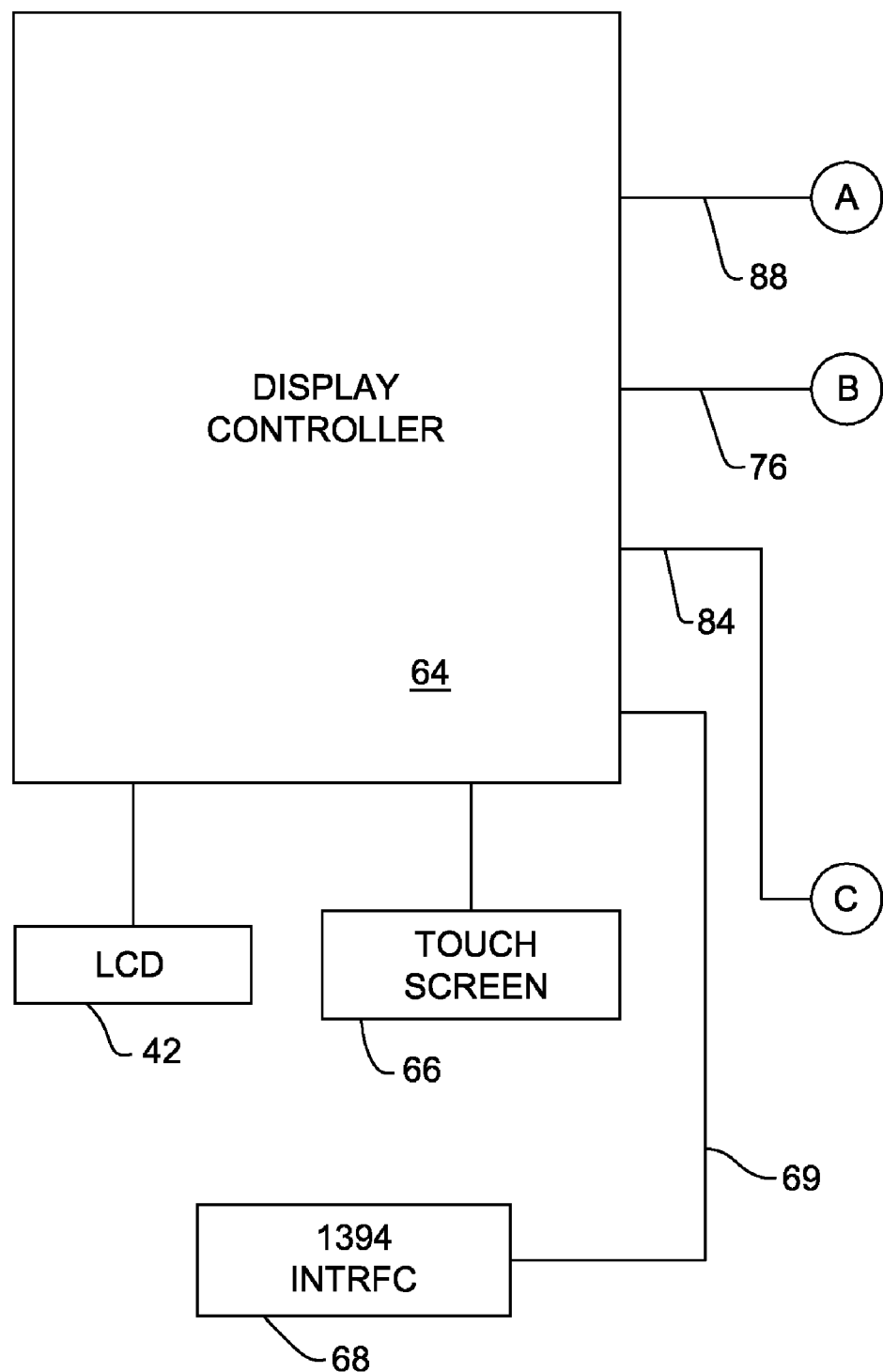
FIGS. 2A and 2B collectively form a block diagram of the major components internal to the control console of the system of this invention.
Figure 2B:
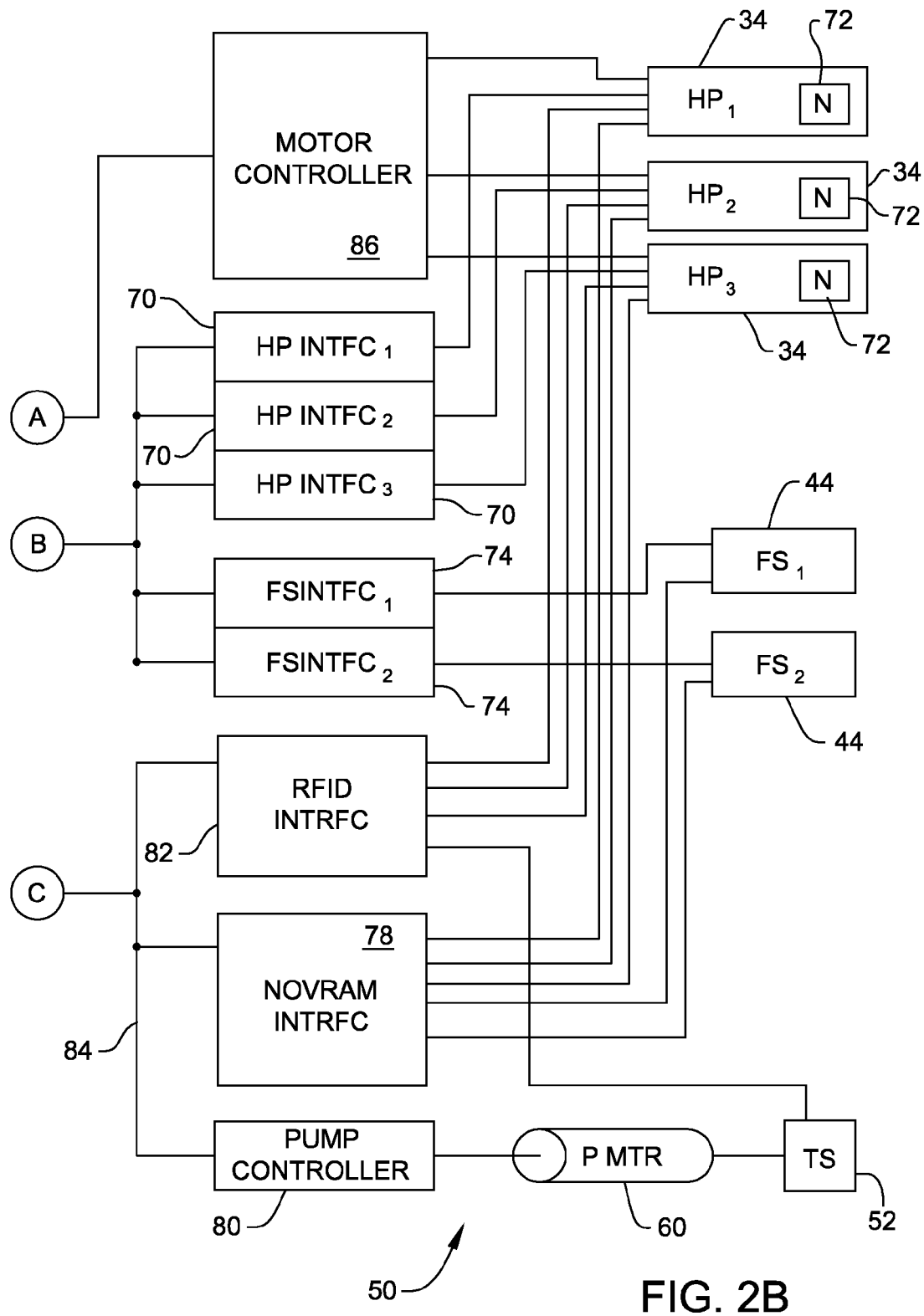

FIGS. 1, 2A and 2B illustrate the basic features of a surgical tool system 30 of this invention. System 30 includes a control console 32. The control console 32 is used to actuate one or more handpieces 34. In FIG. 1, a single handpiece 34, a saw, is illustrated. As seen by reference to FIG. 2B, it is possible to simultaneously connect three handpieces 34, to the control console 32. In the depicted version of the invention, internal to the handpiece 34 is a motor 36 (depicted as a phantom box) and a gear assembly (gear assembly not illustrated). Each handpiece 34 drives a cutting accessory 35 that is typically removably attached to the handpiece. In the illustrated handpiece 34 of FIG. 1, cutting accessory 35 is a saw blade that is removably attached to the distal end of the handpiece. ("Distal" means away from the surgeon/towards the patient. "Proximal" means towards the surgeon/away from the patient.) The illustrated handpiece 34 has a gear assembly designed to oscillate the saw blade back and forth. Other motorized handpieces 34 may be provided with other motor and gear assemblies to drive the associated cutting accessories in rotational movement. It is also recognized that a handpiece 34 typically has coupling assembly, represented by identification number 33 in FIG. 1, that releasably holds the cutting accessory 35 to the handpiece.

Each handpiece 34 is removably attached to a control console 32 by a flexible cable 38. The control console has multiple sockets 40. Each socket 40 is capable of receiving a separate cable 38. This allows the multiple handpieces 34 to simultaneously be connected to the control console 32.

Control console 32 has a display 42 with a touch screen surface. Commands for regulating the components of the system 30 are entered into the control console by depressing buttons presented as images on display 42. Commands are also entered into control console 16 by other control switches. These switches may be integral with the handpieces 34. Alternatively, these switches may be individual switches that are part of a footswitch assembly 44 also attached to the control console 32. In FIG. 1, a single footswitch assembly 44 is shown connected to the control console 32 by a cable 46. Control console 32 is provided with two sockets 48 for receiving two cables 46. This allows two footswitch assemblies 44a and 44b as seen in FIG. 2B to be simultaneously attached to the control console 16.

A pump 50 is also attached to the control console 32. Pump 50 includes a tube set 52 that is removably attached to the control console 32. Tube set 52 includes tubing 54 that provides a fluid path from a bag of irrigation fluid 56 to an irrigation clip 58 attached to the handpiece 34. Pump 50 also includes a motor 60 (FIG. 2B) disposed inside the control console 324.

FIGS. 2A and 2B, when assembled together, illustrate the main components internal to control console 30. These components include a display controller 64. Display controller 64 controls the output of images presented on display 42, represented as LCD (liquid crystal display) in FIG. 2A. The display controller 64 also serves as the overall controller for the control console 32. Thus, the display controller 64 receives the various input signals generated to control the operation of the equipment attached to the console 32. Display controller 64, determines the type of received input signal and, based on this determination, causes the other components internal to the console to generate the appropriate output signals.

Thus, display controller 64 is connected to a touch screen signal processor 66. The touch screen signal processor 66 monitors the depression of the touch screen layer over the display 28. Touch screen processor 66, upon detecting the depression of a portion of the touch screen layer, informs the display controller 64 of which section of the screen was depressed. Display controller 64 uses this information to determine which of the buttons presented on the display 42 was depressed.

Display controller 64 is also connected to a network interface 68, represented as the 1394 Interface in FIG. 2A. Network interface 68 serves as the device over which, by a network (not illustrated), the display controller 68 exchanges information about system 30 with other equipment used to facilitate the performance of the surgical procedure. One such piece of equipment may be a surgical navigation unit. When the control console 32 is connected to this type of component, display controller 64 will inform the surgical navigation unit about the types of handpieces 34, 34, 34 that are connected to the control console and the specific types of cutting accessories attached to the individual handpieces. The surgical navigation unit uses the data to generate information displaying where, on or in the patient's body, the handpieces and cutting accessories are located.

Alternatively, the control console 30 may be connected to a voice recognition surgical control head. This type of device receives the surgeon's voice commands directing the operation of the surgical equipments. Examples of such commands are "Shaver, faster" and "Irrigation, on". In response to receipt of a specific spoken command, the voice recognition control head converts the command into a specific instruction packet. This packet is forwarded to the display controller 64 through the network interface 68.

Display controller 64 and network interface 68 are exchange signals over a dedicated SPI bus 69. Since the display controller 64, as discussed below, regulates the actuation of each handpiece, and commands for handpiece regulation are entered through network interface 68, interface 68 functions as a common interface for entering commands used to regulate the attached handpieces 34.

Control console 32 also includes three handpiece interfaces 70. Each handpiece interface 70, is through a separate one of the sockets 40 and a cable 38 is connected to a separate one of the handpieces 34. Each handpiece interface 70 exchanges signals with components internal to the associated handpiece 34.

Components internal to a handpiece 34 that exchange signals with the handpiece interface 70 are sensors. For example, one handpiece may have a first sensor that monitors the temperature of the motor 36 internal to the handpiece. The same handpiece 34 may have a second sensor that generates an analog signal as function of the displacement of a switch lever on the handpiece. The output signal from this sensor thus represents the surgeon-selected speed for the handpiece motor 36. Another handpiece may have a sensor that generates a signal is a function of the open/closed state of valve that regulates irrigation flow through the handpiece. Based on the state of this valve, the display controller 64 may increase the speed of the pump motor 60 to increase/decrease the rate at which irrigation fluid is supplied to the handpiece 34.

Handpiece interface 70 is also capable of forwarding signals to components internal to the handpiece 34. For example, a handpiece may include a component that emits light, RF waves or an acoustic signal. The signal emitted by this device is used by the surgical navigation system to track the location of the handpiece. The energization signal for that actuates this component is transmitted to from the control console 32 through the handpiece interface 70.

Control console 32 also includes two footswitch interfaces 74. Each footswitch interface 74, through a separate one of the sockets 48 and a cable 46, exchanges signals with a separate one of the footswitch assemblies 44. More particularly, each footswitch 44 includes one or more pressure sensitive sensors that generate signals in response to depression of a specific pad on the footswitch assembly. Each footswitch interface 74 reads the data from the footswitch sensors of the footswitch to which the interface is connected.

The handpiece interfaces 70 and footswitch interfaces 74 are connected to the display controller by a common first UART bus 76.

Control console 32 also includes a NOVRAM interface 78. The NOVRAM interface reads the data in memories internal to the handpieces 34 and footswitch assemblies 44. Specifically, internal to each handpiece 34 that exchanges signals with the handpiece interface is a NOVRAM 72. Each NOVRAM 72 contains data specific to the operation of the handpiece 34 which the NOVRAM is mounted. Examples of such data include the minimum and maximum speeds at which the motor internal to the handpiece should develop, and the maximum torque the motor should produce at a given speed. The handpiece NOVRAMs 72 also contain data that identifies the type of sensors in the handpiece 34 and data that facilitates the processing of the output signals from the sensors. The above-referenced U.S. Pat. No. 6,017,354, which is incorporated herein by reference, offers a more detailed list of types of data stored in the NOVRAM 72.

While not illustrated, it should be understood that each handpiece also contains an EEPROM. NOVRAM interface 78 is capable of reading data from and writing data to the handpiece EEPROMs. The data written to the handpiece EEPROMs include data indicating elapsed time the handpiece 34 has been actuated and data identifying any faults detected during the operation of the handpiece.

Each footswitch assembly 44 also contains a NOVRAM (footswitch assembly NOVRAMs not illustrated). Each footswitch NOVRAM contains data describing the configuration of the associated footswitch assembly 44 and data useful for processing the signals generated by the sensors internal to the assembly.

A pump controller 80 is also incorporated into the control console 34. Pump controller 80, in response to commands from the display controller 64, regulates the on/off actuation of the pump motor 60. The pump controller 80 also regulates the speed at which the pump motor 60 is actuated so as to regulate the rate at which irrigation fluid is discharged from pump 50. In one version of the invention, the primary component about which the circuit forming the pump controller 80 is constructed is the ATmega8 microcontroller available from Atmel Corporation of San Jose, Calif., USA.

Control console 32 also has an RFID interface 82. The RFID interface 32 exchanges signals with any radio frequency identification devices (RFIDs) that are connected to the control console 32 (RFIDs not illustrated). Each RFID contains a memory and a circuit that facilitates the reading of data from and writing of data to the memory. Each cutting accessory 35 attached to an individual handpiece 34 may have an RFID. Each RFID integral with a cutting accessory 35 contains data describing the characteristics of the cutting accessory. These data may describe the physical characteristics of the cutting accessory and/or the speed and direction at which the cutting accessory should be driven. The Applicant's U.S. patent application Ser. No. 10/214,937, SURGICAL TOOL SYSTEM WITH COMPONENTS THAT PERFORM INDUCTIVE SIGNAL TRANSFER, filed Aug. 8, 2002, U.S. Patent Publication No. US 2003/0093103 A1, now U.S. Pat. No. 10/214,937, which is explicitly incorporated herein by reference, provides a detailed instruction of how data in a cutting accessory RFID is used to regulate the actuation of the handpiece 34 to which the cutting accessory 35 is attached.

An RFID may also be attached to either the tube set 52 of the pump 50 or the bag 56 holding the pumped irrigation fluid. The data in the tube set RFID describes the characteristics of the tube set 52. The data in the bag RFID describes the characteristics of the contents of the bag 56. The Applicant's Assignee's U.S. patent application Ser. No. 10/952,410, SURGICAL TOOL SYSTEM WITH INTEGRATED PUMP, filed Sep. 28, 2004, published as U.S. Patent Publication No. US 2006/0073048 A1, which is explicitly incorporated herein by reference, provides a detailed explanation of how the data in the RFIDs within a tube set 52 and a fluid bag 56 are used to regulate the actuation of the pump 50.

The RFID interface 82 reads the data from and writes data to the cutting accessory, tube set and fluid bag RFIDs. Signals are transferred between the RFID interface 82 and the individual RFIDs by inductive signals transfer. Not shown are the coils in the control console 32 that facilitate signal transfer between the tube set 52 and fluid bag 56 RFIDs. Similarly not shown are the coils internal to the handpieces 34 that facilitate the signal exchange between the control console 32 and the cutting accessories 35 attached to the handpieces. RFID interface 82 is constructed out of one or more SL RC400 I-CODE Readers available from Philips Semiconductors of Eindhoven, The Netherlands.

The NOVRAM interface 78, the pump controller 80 and the RFID interface 82, forward data to and receive instructions from the display controller 64 over a second UART bus 84

Control console 32 also includes a motor controller 86. Motor controller 86 is the circuit that, based on instructions from the display controller 64, generates the energization signals to the motors 36 other power-consuming units internal to the handpiece 34. Motor controller 86 is simultaneously connected to the three handpieces through the sockets 40 and cables 38. The motor controller 86 provides data and receives instructions from the display controller 64 over a second SPI bus 88.

Figure 3:
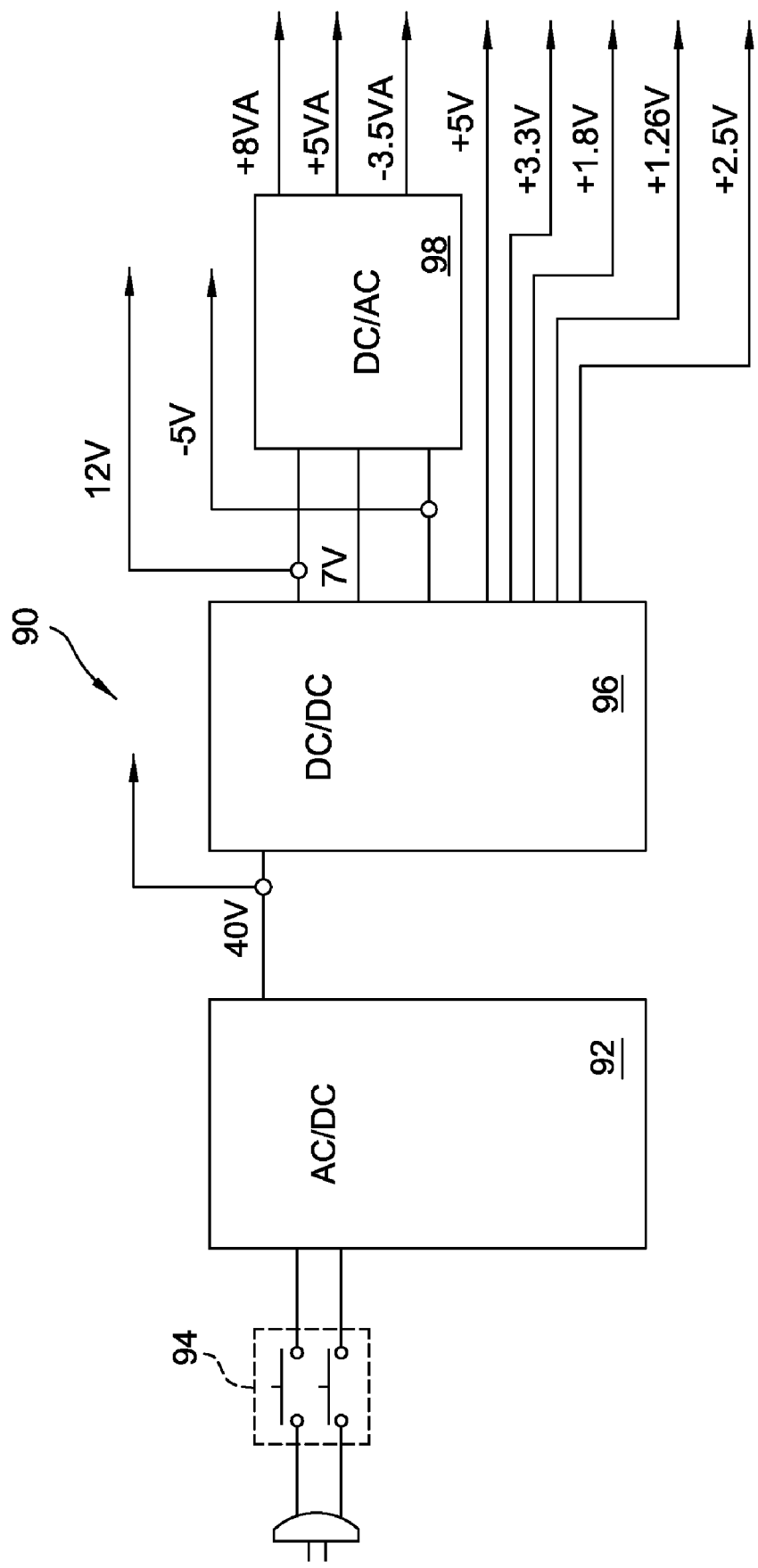
FIG. 3 is a block diagram of the sub-circuits internal to the power supply of the control console.

As seen by reference to FIG. 3, also internal to the control console is a power supply 90. Power supply 90 includes an AC to DC converter 82. The AC/DC converter 92 converts the line signal into a 40 VDC signal. This 40 VDC is the signal applied to the handpiece 34 by motor controller 86. The signal flow of the line voltage into the AC/DC converter is controlled by a single pull double throw switch 94. Switch 94 thus functions as the main on/off switch for the control console 94. Internal to the AC/DC converter are a series of chokes that filter the line signal and a bridge rectifier that converts and filters the line signal into a DC voltage. A UCC38500 power manager available from Texas Instruments of Dallas, Tex., is used to perform power factor correction of the output signal. A boosted DC signal, at 380V, is then pulse wave modulated across a step down transformer. The output signal from the transformer is rectified and filtered to produce the 40 VDC output signal. In order to reduce the complexity of the drawings, unless necessary, the buses along which the 40 VDC signal and the other output signals produced by power supply 40 are not shown.

In addition to being applied to the handpieces 34, the 40 VDC is also applied to a digital power supply 96 also part of the power supply 90. The power supply 96, components not illustrated, converts the 40 VDC signal into a 12 VDC, 7 VDC, 5 VDC, 3.3 VDC, 2.5 VDC 1.8 VDC 1.26 VDC and −5 VDC signals. All of the above signals but the 7 VDC signal are made available on buses for use by other components internal to the control console 32.

The 12 VDC, 7 VDC and 5 VDC signals produced power supply 96 are forwarded to an analog power supply 98, also part of power supply 90. Based on the input signals, power supply 98 produces 8 V, 5 V and −3.5 V precision, constant analog signals. The analog signals produced by converter 98 are used by sensing circuits internal to the control console 32. Power supply 98 also produced a VREF signal. Typically the VREF signal is 2.5 Volts.

Figure 4:
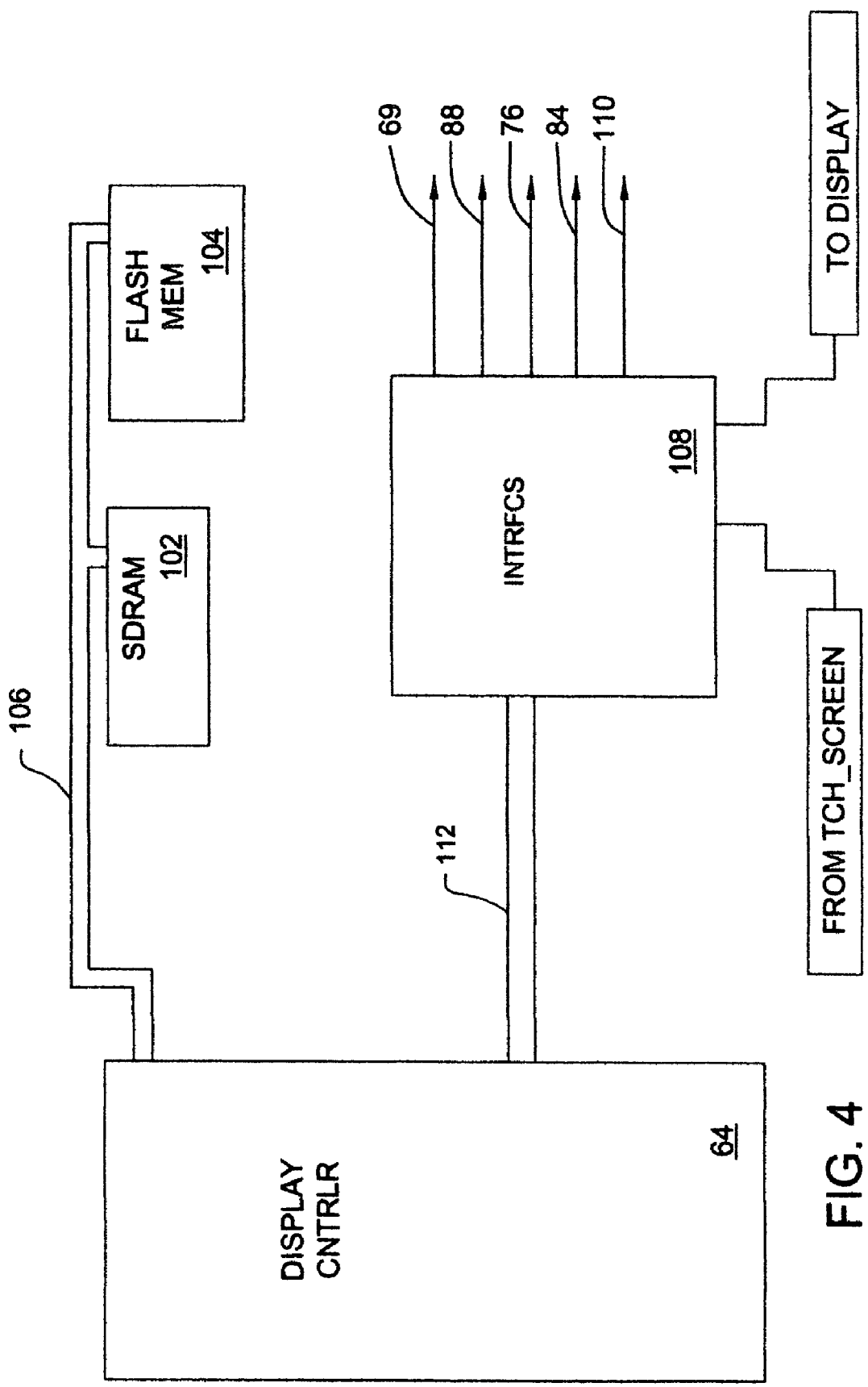
FIG. 4 is a block diagram of the display controller and the components peripheral to the display controller.

Display controller 64 and the components peripheral to it are now described by reference to FIG. 4. The display controller 64 is any suitable microprocessor. One potential microprocessor is the GDPXA255A0C300 processor from the Intel Corporation of Santa Clara, Calif. Both SDRAM 102 and a flash memory 104 are connected to the display controller 64. The SDRAM 102 holds operating instructions and data for run time use by the display controller 64. Flash memory 104 is a non-volatile memory that stores the permanent operating instructions for the display controller 64 and calibration data for touch screen 66. The SDRAM 102 and flash memory 104 are connected to the display controller 64 by a common bus 106.

A collection of sub-circuits, broadly referred to as interface 108, are also connected to display controller 64. Internal to interface 108 are the individual sub-circuits that control the exchange of signals between the display controller 64 and the buses internal to the other components within control console 32. These sub-circuits include the circuits that facilitate the exchange of signals over the two SPI buses 69 and 88, the UART buses 76 and 84 and with the display 42 and touch screen signal processor 66. Interface 108 also includes a circuit for facilitating signal exchange over a USB bus 110 internal to the control console 32.

Signals are exchanged between display controller 64 and the sub-circuits forming interface 108 over a collection of conductors generally identified as bus 112. It should be recognized that the exchange of signals between the display controller and the individual sub-circuits forming interface 108 is, between the sub-circuits, asynchronous.

A number of additional peripheral devices, while not illustrated should further be understood to be connected to display controller 64. These parts include a crystal that provides a clock signal to the display controller 64. There are circuits that provide a stable power supply and short life back-up power supply to the display controller 64 and the sub-circuits forming interface 108.

When system 10 of this invention is initially set up to run, display controller 64 reads the data in the handpiece NOVRAMs 72, the footswitch assembly NOVRAMs, and the RFIDs' internal to the cutting accessories 35 and the pump tube set 52. Based on these data as well as any additional data entered by the operating room personal, the system is configured for operation. For example, absent any additional instructions, based on the data received from a handpiece NOVRAM 72 and the RFID of the complementary cutting accessory 35 attached to the handpiece, display console 64 establishes for the handpiece the speed range in which its motor 36 should operate and preferred or default speed. This latter speed is the initial operating speed of the motor if it is operated at single speed. Display controller will also cause to be presented on display 42 an image that identifies the handpiece and cutting accessory combination.

Based on data read from the footswitch assembly NOVRAM, display controller 64 determines what correction factors need to be provided to the analog input signals generated by the sensors internal to the assembly. Based on data from the RFID internal to the pump tube set 52, the display controller 64 establishes the speed at which the pump motor 62 should run in order to discharge irrigation fluid at a specified flow rate.

Once the system 10 is configured for operation, surgeons actuate the various components, i.e., the handpieces 34 and pump 50 by entering commands into the control console 32. These commands may be entered by depressing pedals on the footswitch assemblies 44 or by depressing control buttons on the handpieces 34 or that are presented on display 42. Spoken commands may also be entered with a voice recognition surgical control head through network interface 68. Based on these commands, display controller 64 sends specific commands to the components internal to the control console. Primarily these commands are sent to motor controller 86 to actuate one or more of the handpieces 34. Display controller 64 and motor controller 86 can thus be considered a common control unit that regulates the application of energization signals to the individual handpieces 34. Some commands are sent to the pump controller 80 to actuate the pump motor 60.

Figure 5:
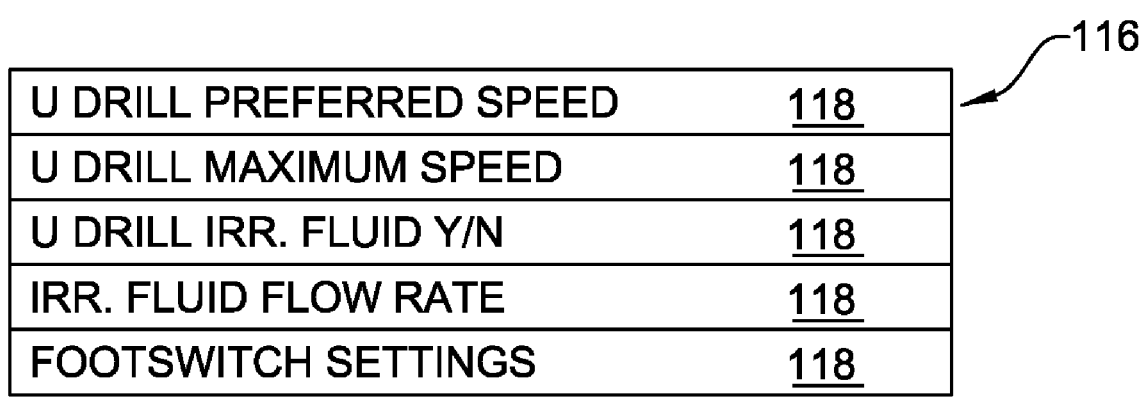
FIG. 5 depicts the records contained within an exemplary procedure preference file.

Internal to flash memory 104 associated with the display controller 64 are a number of procedure preference files 116, one of which is now described by reference to FIG. 5. Each procedure preference file 116 indicates how, as an alternative to the default settings, one or more components of the system 10 are to be configured for operation during a specific surgical procedure. Each procedure preference file 116 contains one or more component preference fields 118. Each preference field contains two sub-fields, (not identified). The first sub field includes data identifying the component to be configured, the second sub field identifies how the component is to be configured.

In the illustrated preference file 116, the first component preference field 118 contains data indicating that the preferred setting, the initial setting for the speed of a universal drill handpiece is to be set at rate different than the default setting in the handpiece NOVRAM 72. The second component preference field 118 contains data indicating the maximum speed for the universal drill handpiece is to be set at a rate different than the rated maximum speed specified by NOVRAM 72. (This alternative maximum speed is less than the rated maximum speed.) The third component preference field 118 contains data indicating whether or not the pump 50 is to be actuated when the handpiece 34 is actuated. Data regarding the preferred flow rate at which the pump 50 is to be actuated are stored in the fourth component preference field 118. The fifth component preference field 118 contains data regarding which individual footswitch pedals should be mapped to control the operation of the handpiece 34 and pump 50.

Figure 6:
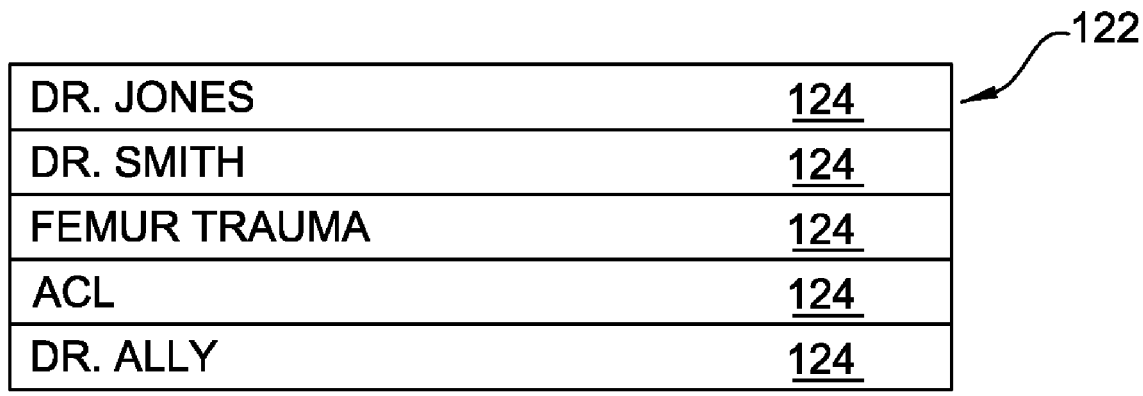
FIG. 6 depicts the records contained within an exemplary master users directory.

Preference files 116 may be established for specific procedures, for specific surgeons and for specific procedures performed by specific surgeons. Specifically, as seen by reference to FIG. 6, display controller 64 stores in memory a master user directory 122. User directory 122 includes a number of user fields 124 each of which contains data that identifies a specific individual surgeon or procedure. The first two and fifth user fields 124 of FIG. 6 identify specific surgeons. The third and fourth user fields 124 identify specific procedures.

Each user field 124 links to a specific preference directory 126, described with reference to FIG. 7. The depicted preference directory 126 is for a specific doctor. Internal to the preference directory 126 are preference fields 128 that identify the procedures for which this doctor has certain instrument preferences. Each preference field thus contains data identifying a procedure for which the doctor has established a preference and data identifying the specific preference file 116 for that procedure. The preference directory 126 for a procedure, identifies the system settings individual surgeons have for the procedure. Each preference field 128 within the directory thus identifies both the doctor and contains a pointer to that doctor's specific preference file 116 for the procedure.

Display controller 64 of this invention also maintains an active preference table 130, described by reference to FIG. 8. Active preference table 130 contains records of four system setting preferences it is system setting preference is stored in a separate active preference file 132. Each active preference file 132 identifies the specific active preference and contains a pointer to the specific preference file 116. The selective active setting preferences can be set on as needed basis.

Figure 9:
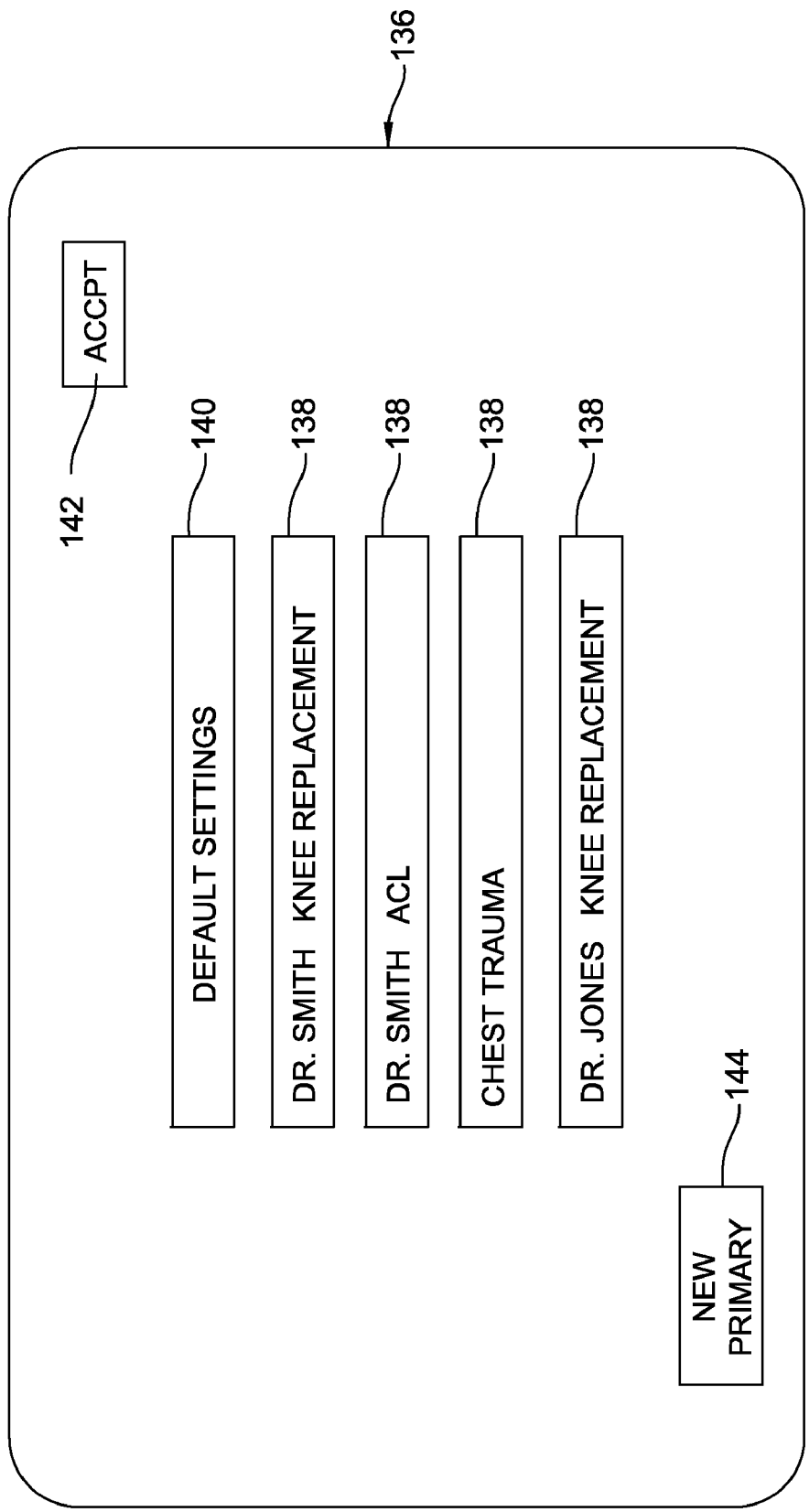
FIG. 9 depicts the image presented on the display to invite the selection of an active preference.

When the system is set to run, operating personnel can relatively easily access an active preferences image 136 on display 42 now described by reference to FIG. 9. The active preferences image 136 includes four bars 138 on which the active preferences stored in table 130 are listed. Also presented is a default bar 140. The operating room personnel can then press one of the bars 138 or 140 to select a particular preference. Confirmation of the acceptance is performed by depressing the accept (ACCPT) button 142. Once the selected setting preference is confirmed, display controller 64 configures the system according to the data in the file 116 for the selected preference.

Alternatively, selection and confirmation of the default setting results in the display controller 64 configuring the system based on the default settings for the handpieces 34 and cutting accessories 35.

Replacement of one of the active preferences is initiated by selecting the preference and depressing the NEW PRIMARY button 144.

An advantage of the above feature of the system 10 of this invention is that it eliminates the need, for commonly used system configurations, to have to go through a longer multi-step selection process to retrieve the data in a specific preference file 118.

System 30 of this invention is further configured so that either footswitch assembly 44 can be used to control any one of the handpieces 34 connected to the control console 32. In order for system 30 to perform this function, it should be understood that the display controller 64 maintains a table 150, illustrated by FIG. 10, for each footswitch assembly 44. The individual fields 152 in table identify the control function assigned to a separate one of the pedals integral with the footswitch assembly. In the depicted version of the invention, footswitch assembly has five pedals. Therefore, table 150 for the footswitch assembly has five pedal assignment fields 152. Display controller 64 writes data identifying the function assigned to each footswitch pedal into its complementary assignment field 152 based on either entered established default settings, manually entered preference commands or data regarding an individual surgeon's preference that are retrieved from storage.

When a signal is received from one of the footswitch sensors indicating the complementary pedal has been actuated, display controller 64, based on reference to the data in table 150 for the footswitch, generates the appropriate command to cause the appropriate state change of the other component connected to the system.

Display controller 64 also updates the data in the footswitch function tables to facilitate the switching of control of the handpieces to between the footswitches as discussed below.

Specifically, the display controller 64 monitors whether or not a handpiece cable 38 is connected to each socket 40 and whether or not a footswitch cable 46 is connected to each socket 48. It is assumed that if a cable 38 is connected to a socket 40, a handpiece 34 is connected to the distal end of the cable 38. Each footswitch assembly 44 is integrally attached to a cable 46. Therefore, the connection of a cable 38 to the control console automatically results in the connection of a footswitch to the console.

Figure 11:
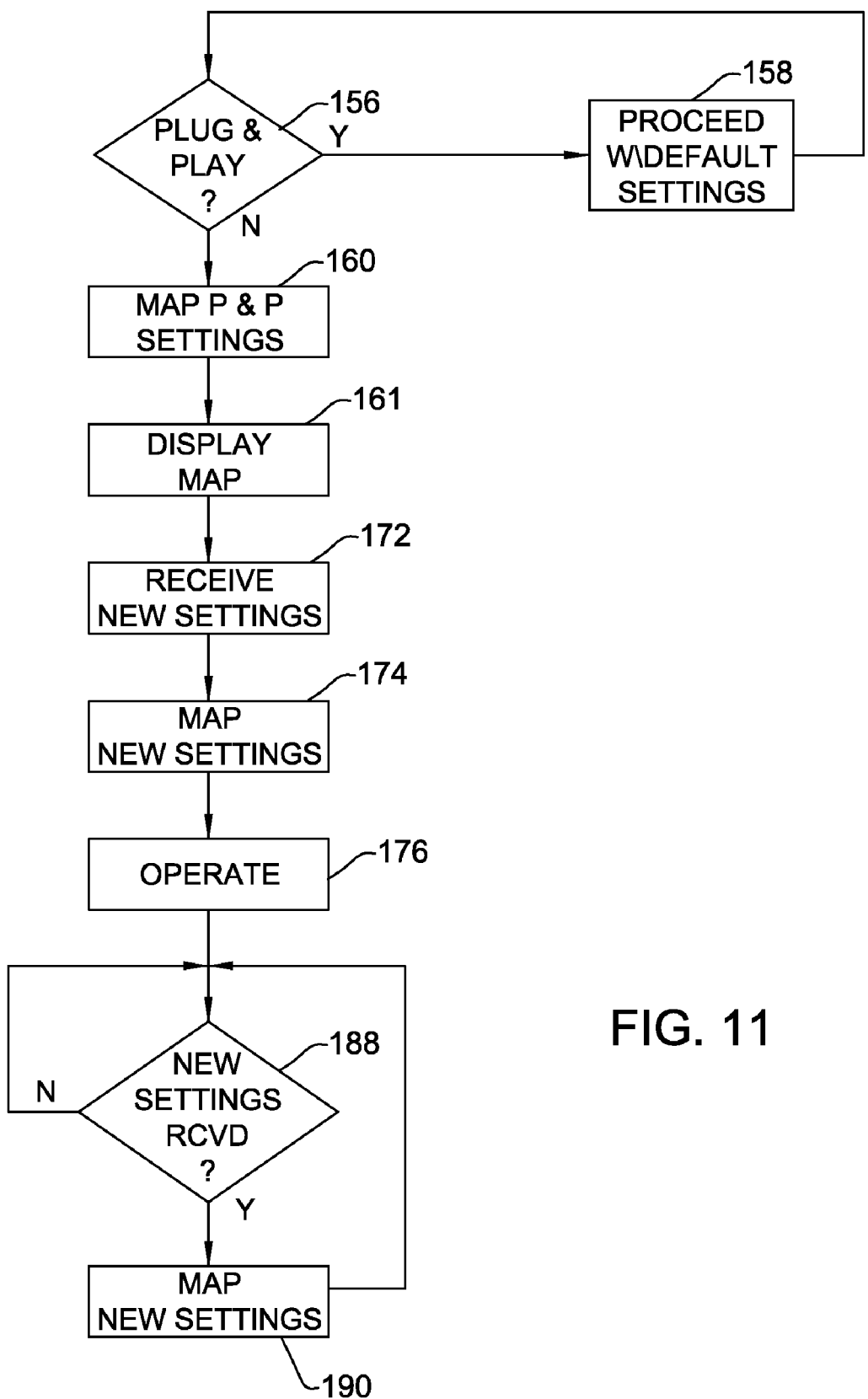
FIG. 11 is a flow chart of the basic process steps used by the control console to assign the footswitches control of the handpieces coupled to the control console.

As represented by step 156 in the flow chart of FIG. 11, the initial monitoring of the handpiece 34 and footswitch 44 connections to the control console 32 is referred to as monitoring whether or not the system 30 is in the plug and play mode. System 30 is considered in the plug and play mode if, at a given time less than two handpieces 34 or less than two footswitch assemblies 44 are connected to the control console 32.

If the system is in the plug and play mode, display controller 64, in step 158, assigns that handpieces to the footswitches according to a default scheme. Specifically under this scheme, if there is just a single footswitch assembly 44 attached to the control console 32, the control of each attached handpiece 34 is assigned, or mapped, to that footswitch. Thus, for each attached handpiece 34, display controller 64 writes to the pedal assignment table 150 for the footswitch assembly 44 data in one of the function fields 152. These data indicate that the footswitch pedal associated with the function field 152 controls the specific handpiece.

Similarly, the system 30 is considered in the plug and play mode when there are plural footswitch assemblies 44 and a single handpiece 34 attached to the control console 32. Display controller 64 performs default mapping for this version of the plug and play mode by mapping control for the handpiece to each footswitch assembly. Thus the display controller 64 writes into the pedal assignment tables 150 for both handpieces data indicating that each footswitch can control the handpiece 34. When both footswitches can control a handpiece, the handpiece is considered to be the below discussed dual-control state.

If, as a result of the cable connection monitoring of step 156, display controller 64 determines that two or more handpieces 34 and both footswitch assemblies 44 are connected to the control console 32, the system is considered to be in the multiples mode. Initially, when the system 30 enters the multiple mode, display controller 64 maps the footswitch assignments to what they were in the immediate past plug and play mode, step 160. Thus, if a single footswitch assembly 44 was controlling the plural handpieces, that footswitch assembly initially retains control of those handpieces. If both footswitch assemblies had a single handpiece under dual control, both footswitch assemblies maintain this control.

Figure 12:
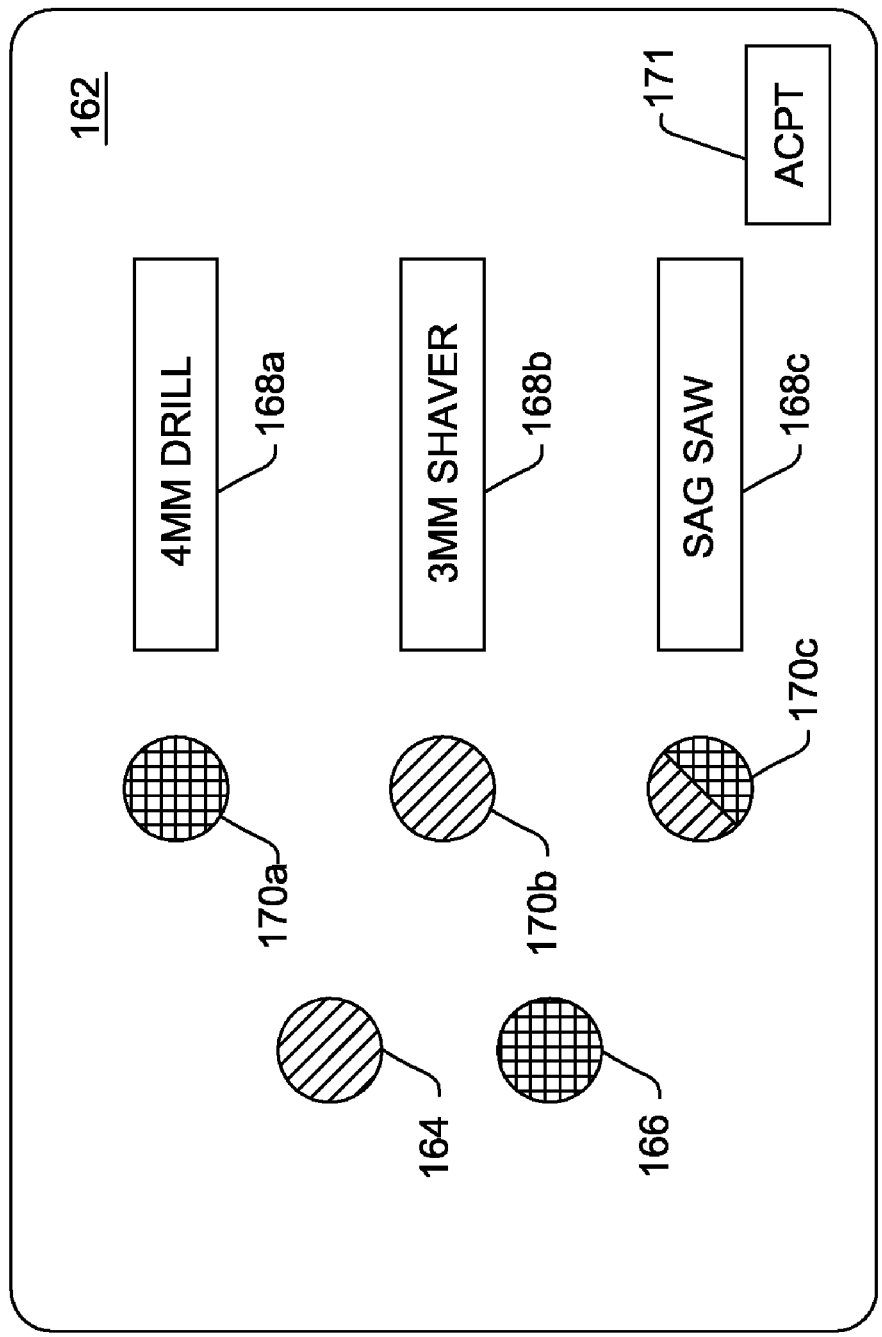
FIG. 12 is a diagram depicting a basic footswitch mapping image that is presented on the control console display.

After the mapping of step 160 is complete, display controller 64, in step 161, causes a footswitch assignment map 162 to be presented on the display 42, as illustrated by FIG. 12. On map 162, each footswitch assembly is represented by a different color button on the left side of the image. In the displayed map a green button 164 is used to represent a first footswitch assembly; a yellow button 166 represents the second footswitch assembly. Legends 168a, 168b and 168c identify each handpiece connected to the control console 34. The data identifying each handpiece so this information can be presented in map 162 is from the handpiece NOVRAMs 72.

Also present on the image of map 162 are color-specific buttons 170a, 170b and 170c that identify to which footswitch assembly 44 each handpiece is presently assigned. Each button 170a, 170b and 170c is immediately to the right of the legend image 168a, 168b and 168c, respectively, of the handpiece with which the button is associated. The color of each button 170a, 170b and 170c corresponds to the color associated with the footswitch assembly 44 presently mapped to control the button's handpiece. Map image 162 of FIG. 12 indicates that the 4 mm drill is under the control of the yellow footswitch assembly, the footswitch assembly connected to the bottom of the two sockets 48.

As represented by button 170c of map 12, a handpiece being under dual control is shown by its associated button being half one color and half the second color.

The surgeon then indicates what footswitch assignments are wanted for the present operation, step 172 of FIG. 11. This step is performed by depressing the touch screen image of each legend 168a, 168b or 168c of each handpiece 34 that is to be mapped to a new footswitch assembly 44. Upon each depression of the legend image, display controller 64 changes the footswitch mapping for the handpiece. Specifically, the display controller cycles the mapping through the following sequence: footswitch assembly associated with upper socket 48; footswitch assembly associated with lower socket 48; dual control mode; and no footswitch control. As the mapping changes, the color of the button 170a, 170b, or 170c changes appropriately to indicate the new assignment for the associated handpiece.

As mentioned above, it is possible to separate a handpiece 34 from footswitch control. This option may be selected for example, when the surgeon chooses to use a handpiece mounted switch to regulate the actuation of the handpiece 34. When this option is selected, the associated button 170a, 170b or 170c on map 162 is presented as a grey. Acceptance of specific footswitch assembly assignment map is performed depressing the image of the accept (ACPT) button 171 also presented of the image of map 162.

It should be understood that the footswitch assignment mapping can only be performed by pressing buttons presented on display 42. This prevents inadvertent depression of the footswitch pedals for unintentionally serving to transfer control of a handpiece 34 from one footswitch assembly 44 to the second footswitch assembly 44.

In response to the surgeon performing step 172, display controller, in step 174 maps the new footswitch assignments into the footswitch assignment tables 150. The surgeon(s) is(are) then able to use actuate each handpiece 34 by depressing the appropriate pedal on the footswitch assembly 44 assigned to control that handpiece, step 176.

Figure 13:
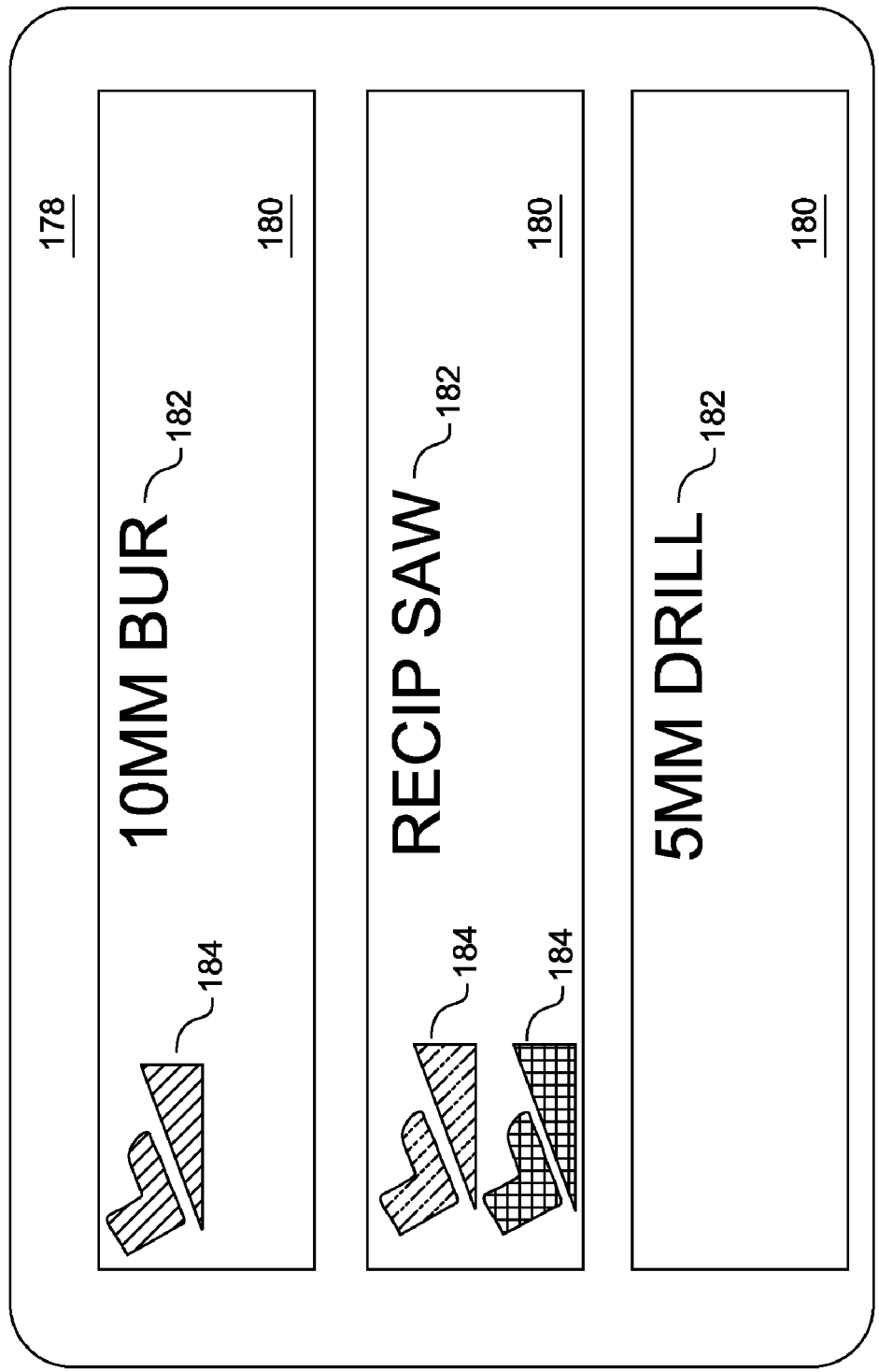
FIG. 13 is a diagram depicting components of the run time image presented on the control console display.

In order to allow operating room personnel to readily keep track of which, if any, footswitch assembly 44 controls a specific handpiece 34, information about this relationship is presented on the run time display 178, depicted in FIG. 13. Specifically, a bar 180 is presented for each handpiece connected to control console. Integral with each bar 180 is a legend 182 that identifies the handpiece. On the right side of the bar 180 a footswitch icon 184 appears if the handpiece is under footswitch control. The color of the icon 184 identifies the footswitch assembly 44 controlling the handpiece 34. In FIG. 13, a green icon 184 is presented with the 10 mm bur bar 180. This means the green footswitch assembly 44 controls this instrument. Both a green icon 184 and a yellow icon 184 are presented with the bar associated with the reciprocating saw bar 180. This means that this instrument is in the below described dual control mode. However, one icon 184 is displayed at full brightness, here the yellow icon; the second icon, here the green icon 184, is displayed at reduced brightness (represented by the phantom presentation). This means that at, the present instant, the yellow footswitch assembly has control of the saw.

In FIG. 13 there is no footswitch icon within the 5 mm drill bar 180. This serves as indication this handpiece 34 is not under the control of either footswitch assembly 44.

Once the desired footswitch assembly 44 assignment maps have been entered into the control console 32, the surgeons can then perform the procedure, represented by step 186

During the course of a surgical procedure, there may be movement of the surgeons, handing off of the handpieces 34 between surgeons or movement of the footswitch assemblies 44. As a result of any one of these events, there may be confusion regarding which surgeon is using which footswitch assembly 44 to control which handpiece 34. If this confusion arises, surgeons can easily place the handpieces in an up position, away from the patient, and actuate each handpiece. As each handpiece is actuated, the run time image changes to show which handpiece is running. This provides the surgeons with a quick means to determine which footswitch assembly 44 is controlling which handpiece 34.

Once the operation begins, the map assignments for the footswitch assemblies 44 may be changed as represented by step 188. Specifically, by depressing other buttons presented on display 42, it is possible to have display controller 64 represent the image of the footswitch assignment map 162. The new footswitch assembly 44 assignments are then entered. These assignments are then mapped into the footswitch assignment tables 150, step 190. System 10, with the new footswitch assemblies assignments, is again available for use.

Figure 14:
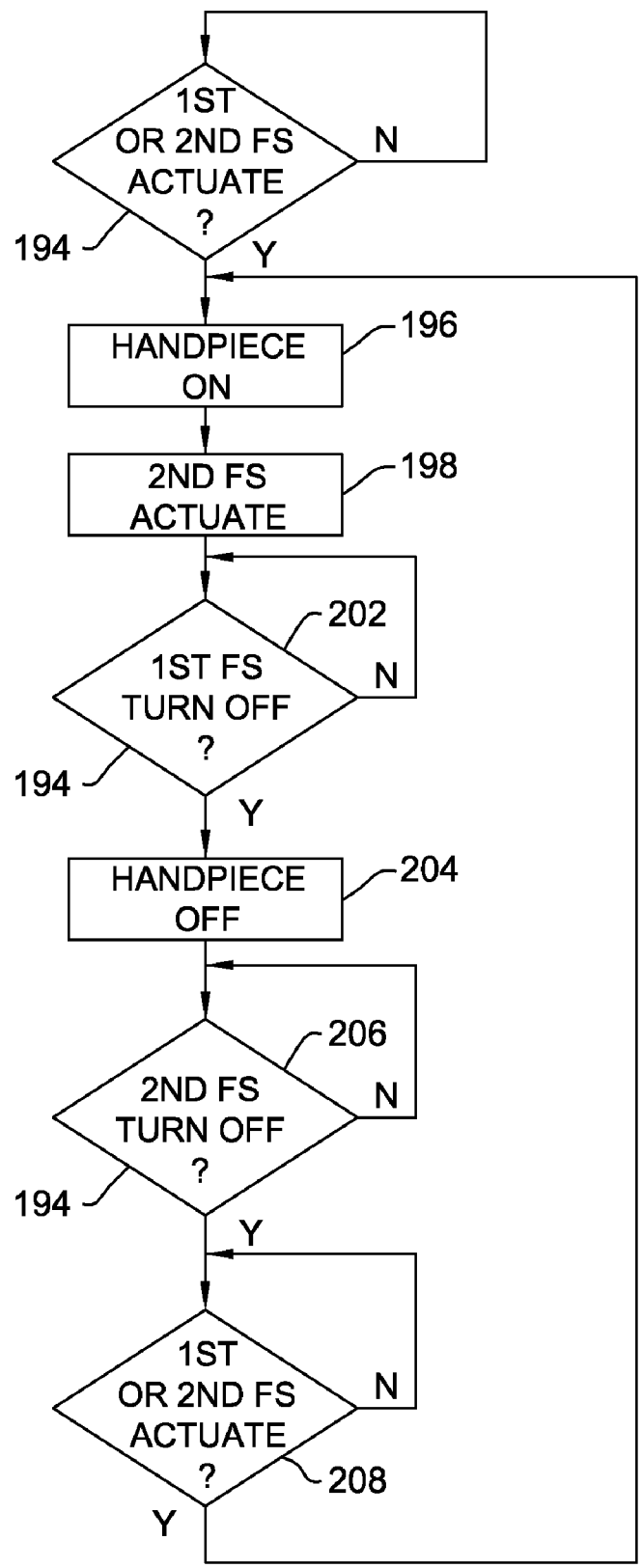
FIG. 14 is a flow chart of the process steps performed by the control console when a handpiece is placed in the dual control mode.

As mentioned above whether the system is in either the plug and play mode or the multiples mode, there may beta situation when one or more of the handpieces 34 are placed in the dual control mode. When a handpiece 34 is in this mode, the depression of an assigned foot pedal on either footswitch assembly 44 will actuate the handpiece. When a handpiece 34 is in this mode, display controller 64 executes the process steps of FIG. 14 to prevent both footswitch assemblies 44 from simultaneously controlling the handpiece. Initially as represented by step 194, display controller 64 monitors the output signals from both footswitch assemblies 44 to determine if either assembly actuates a handpiece under dual control.

If, in step 194, an actuation signal is received from either footswitch assembly 44, display controller 64 instructs motor controller 86 to actuate the handpiece, step 196. Also in step 196, the run time display 178 is changed so as to brighten the image of the icon 184 associated with the activating footswitch assembly 44.

The surgeon using the actuating footswitch assembly 44 may then press the pedals so as to instruct the control console 32 to turn off the handpiece 34. If this event occurs, the display controller causes the handpiece to be deactivated. The display controller 64 returns to step 194. (Above steps not shown.)

However, during step 196, the surgeon operating the second footswitch assembly 44 may attempt to turn the handpiece on, as represented by step 198. Display controller 64 ignores this signal. Instead, as represented by step 202, display controller waits to receive from the first footswitch assembly signals indicating the handpiece is to be turned off. Upon receipt of this signal, in step 204, display controller 64 turns off the handpiece. Display controller 64 takes this action even though the second footswitch assembly is still generating a command calling for the handpiece to be actuated. Also as part of step 204, display controller dims the intensity of the icon 184 associated with the actuating footswitch assembly 44. At this time both footswitch icons 32 associated with the handpiece under dual control are in dim state. This provides operating room personnel with an indication that, at the present time, neither footswitch assembly 44 has control of the handpiece 32.

Instead, as represented by step 206, waits to receive a signal from the second footswitch assembly 44 to turn off the handpiece 34. Until this signal is received, display controller 64 prohibits either footswitch assembly 44 from actuating the handpiece 34.

Once, in step 206, a signal is received from the second footswitch assembly to turn off the handpiece, display controller is able to execute step 208. In step 204, display controller again monitors the output signals from both footswitch assemblies 44 to determine if either of them have turned on the handpiece 34. Thus, step 208 is essentially identical to first described step 194. Once this type of signal is received, display controller 64 reexcutes step 196 to reactuate the handpiece 34.

Figure 15A:
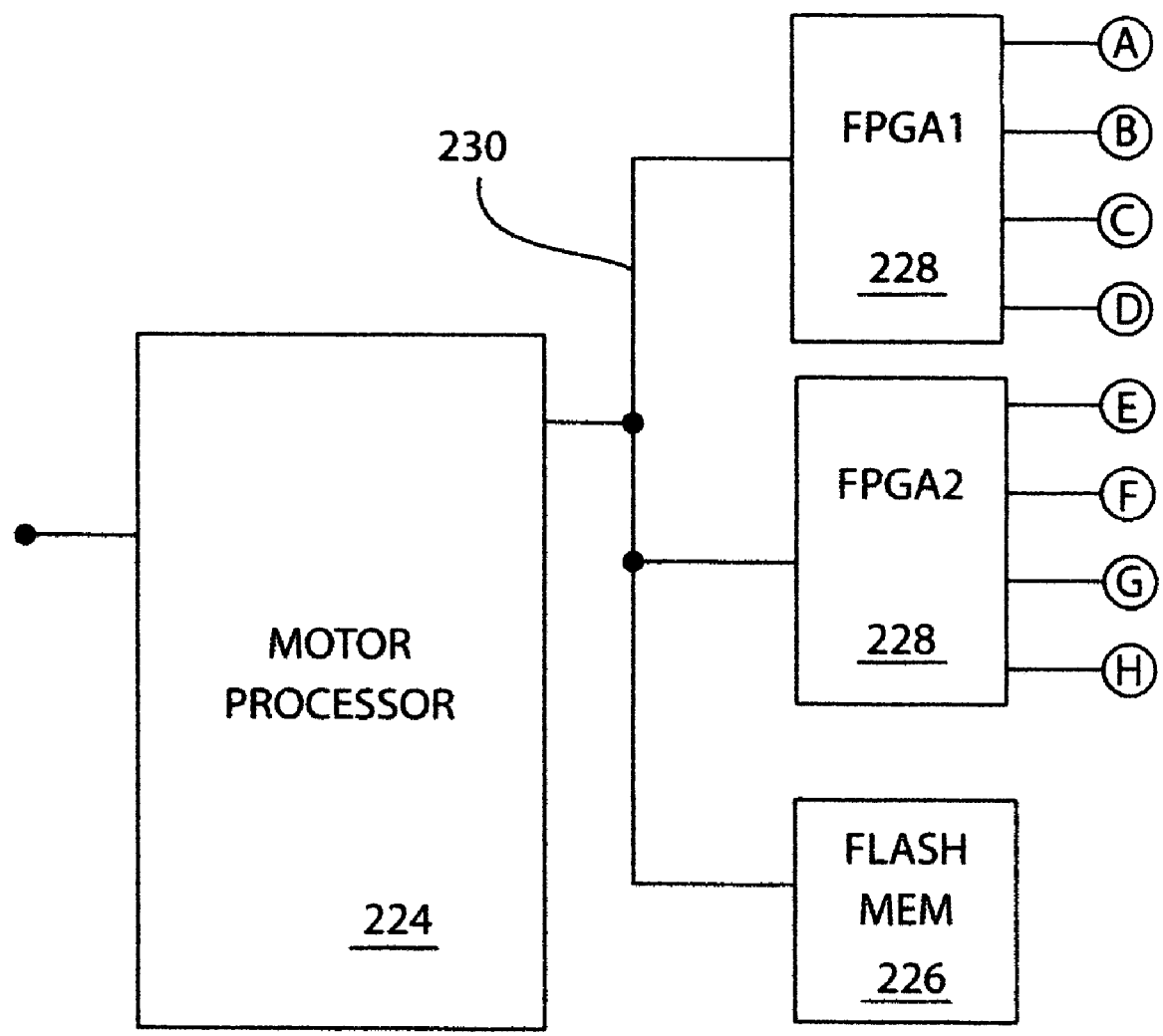
FIGS. 15A and 15B, when assembled together, form a block diagram of the main components of the motor controller.
Figure 15B:
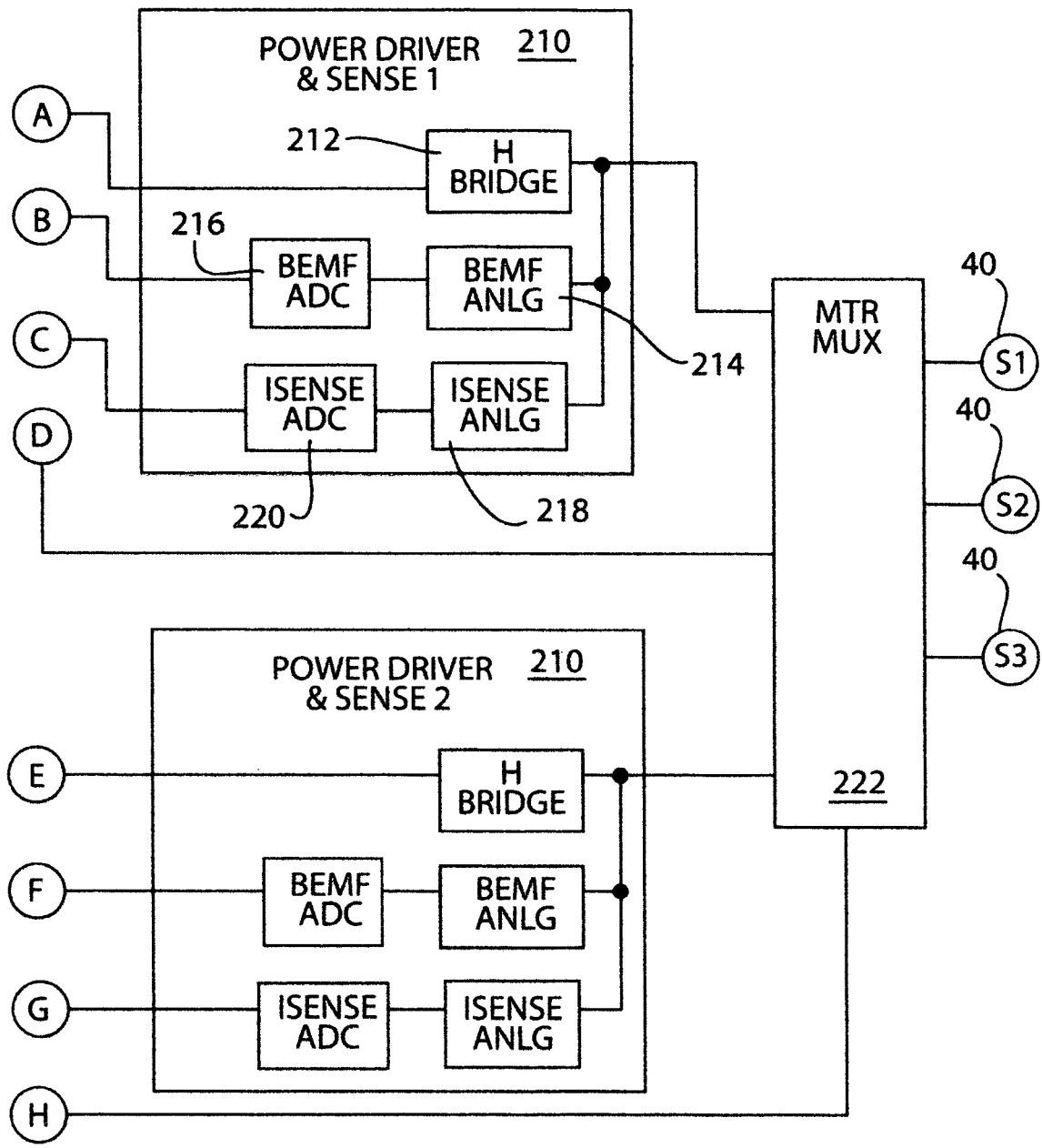

Motor controller 86 is now generally described by reference to FIGS. 15A and 15B. Specifically, the motor controller 84 includes two identical power driver and sense circuits 210. Each power driver and sense circuit 210 is capable of supplying the power to the motor 36 of any handpiece 34 connected to any one of the sockets 40. (In FIGS. 15B and the following figures, the individual sockets 40 are identified as S1, S2 and S3.) Specifically, internal to each power driver and sense circuit is an H bridge 212. The H bridge is the sub circuit that selectively ties each winding of the connected to either the 40 V power line or ground.

The power driver and sense circuit 210 also monitor signals generated as a consequence of the actuation of the handpiece motors. In order to perform this monitoring, each circuit 210 has a BEMF analog circuit 214 The BEMF analog circuit extracts the BEMF signal produced across the unenergized winding internal to the motor. A BEMF analog to digital circuit 216 converts the extracted BEMF signal to a digital signal. AN ISENSE analog circuit 218 monitors the currents drawn by the handpiece motor 36 as well as currents internal to the control console 32. An ISENSE analog to digital circuit 220, also internal to circuit 210, converts the signals representative of the monitored currents into digital signals.

The power signals, the energization signals, to the motor windings output by the H bridges 212 are applied to a motor multiplexer 222. Motor multiplexer 222 is capable of generating the power signals generated by H bridge 212 to any one of three sockets 40.

A motor processor 224, also part of the motor controller 86, regulates the operation of the power driver and sense circuits 210 and the motor multiplexer 222. In some preferred versions of the invention, a DSP processor is employed as the motor processor 224. One processor from which motor processor 224 can be constructed is the TMS320C6713 floating-point digital signal processor available from Texas Instruments of Dallas, Tex. Certain data used by motor processor 224 are written to and read from a flash memory 226. One such flash memory is available the Intel Corporation. Data stored in flash memory 226 include the instructions executed by motor processor 224, configuration data for the FPGAs 228 and calibration data for the current sensing circuits.

The actual control signals generated to the power driver and sense circuits 210 are generated by field programmable gate arrays (FPGAs) 228. Each FPGA 228, in response to instructions from the motor processor 224, generates control signals to a separate one of the motor driver and sense circuits 210. Each FPGA 228 also receives the digitized BEMF and sensed current signals from the circuit 210 to which the FPGA is connected. The FPGAs 228 also control the settings of motor multiplexer 222. Suitable FPGAs can be manufactured from the XC2S3x Spartan Series programmable gate arrays available from the Xilinx Corporation of San Jose, Calif.

Motor processor 224 is connected to the flash memory 226 and the FPGAs 228 by a parallel bus 230. (Bus 230 shown as a single line in FIG. 15A.).

Figure 16A:
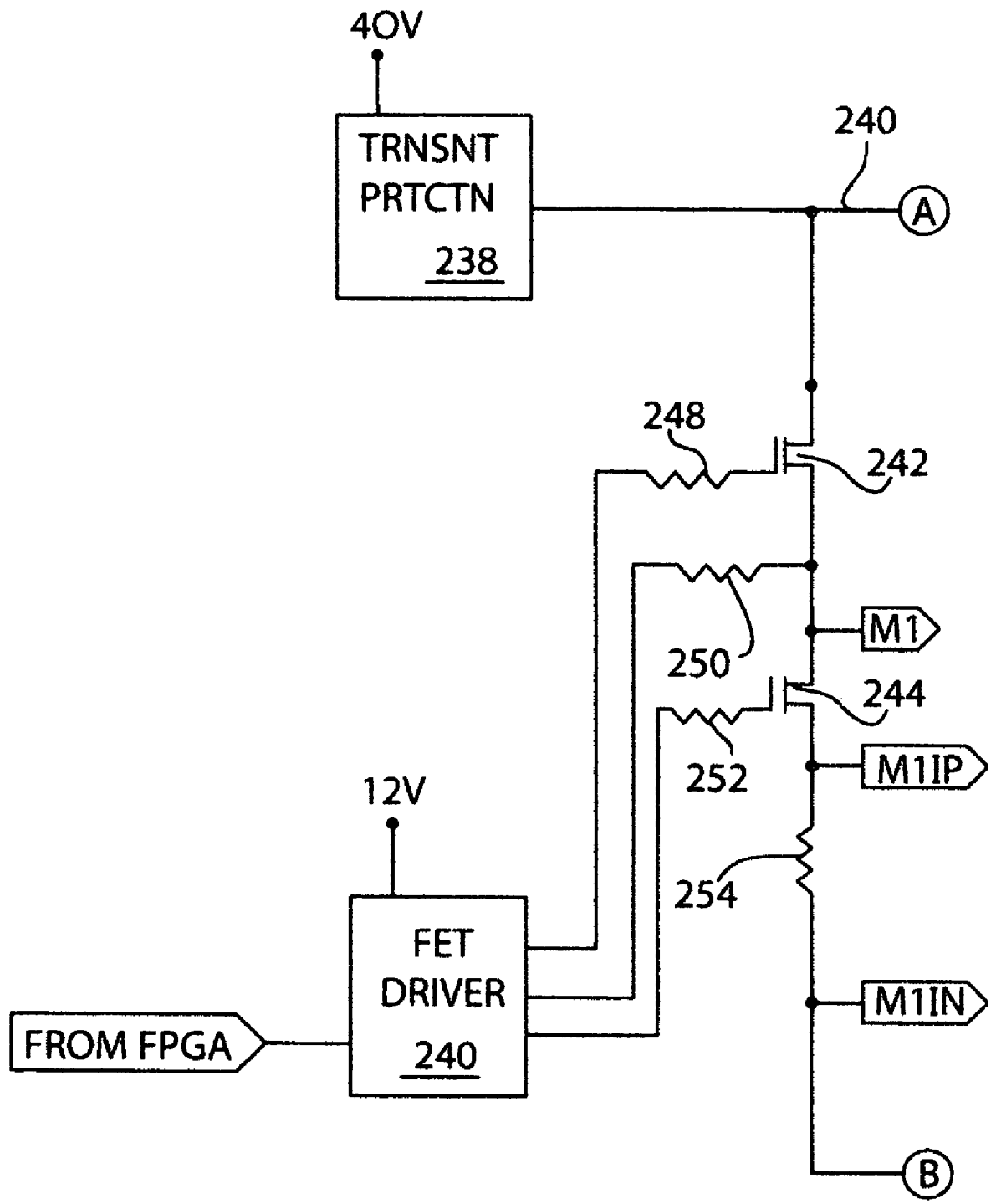
FIGS. 16A, 16B and 16C, when assembled together form a block and partial schematic diagram of the H bridge of the motor controller.
Figure 16B:
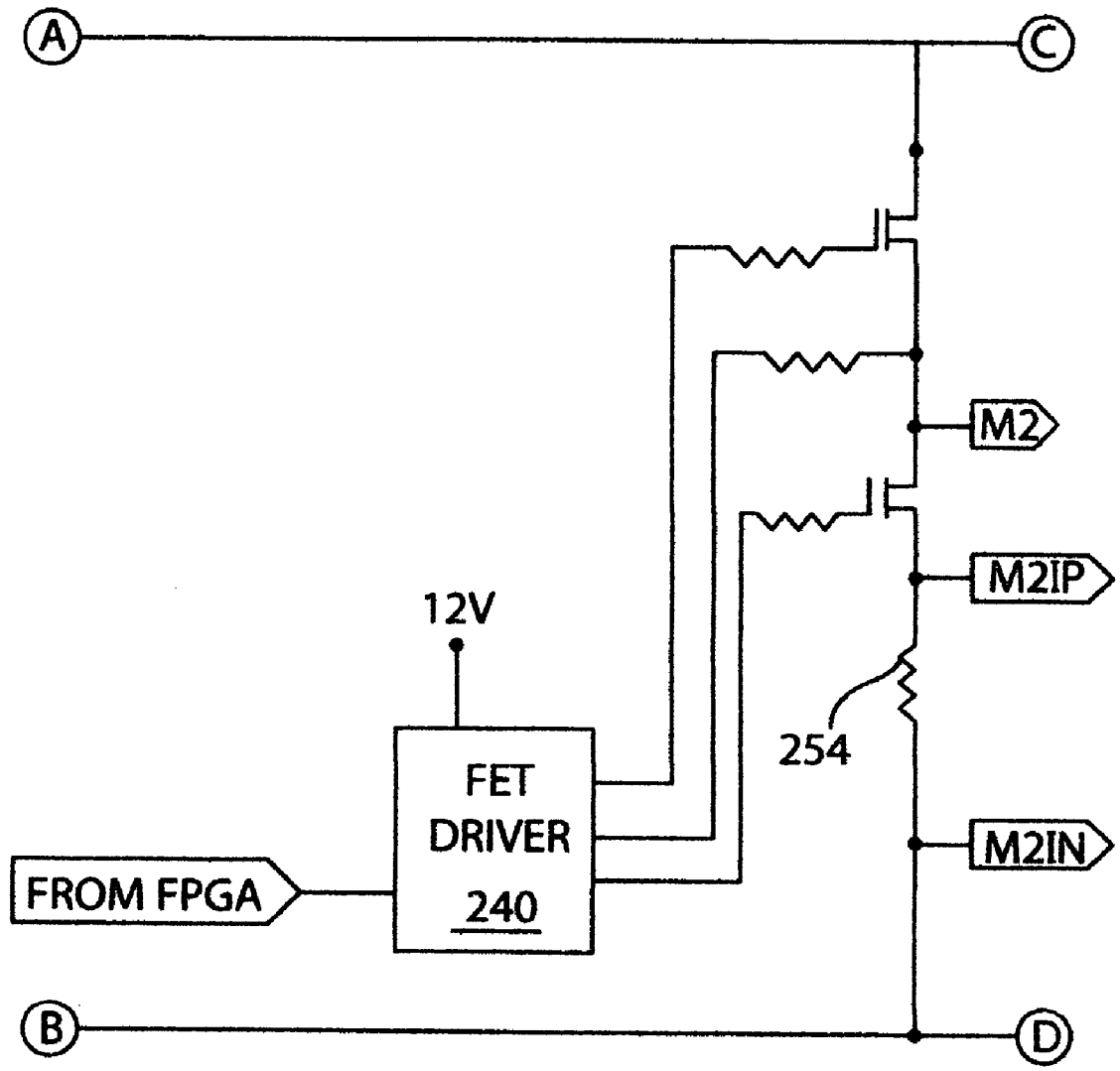
Figure 16C:
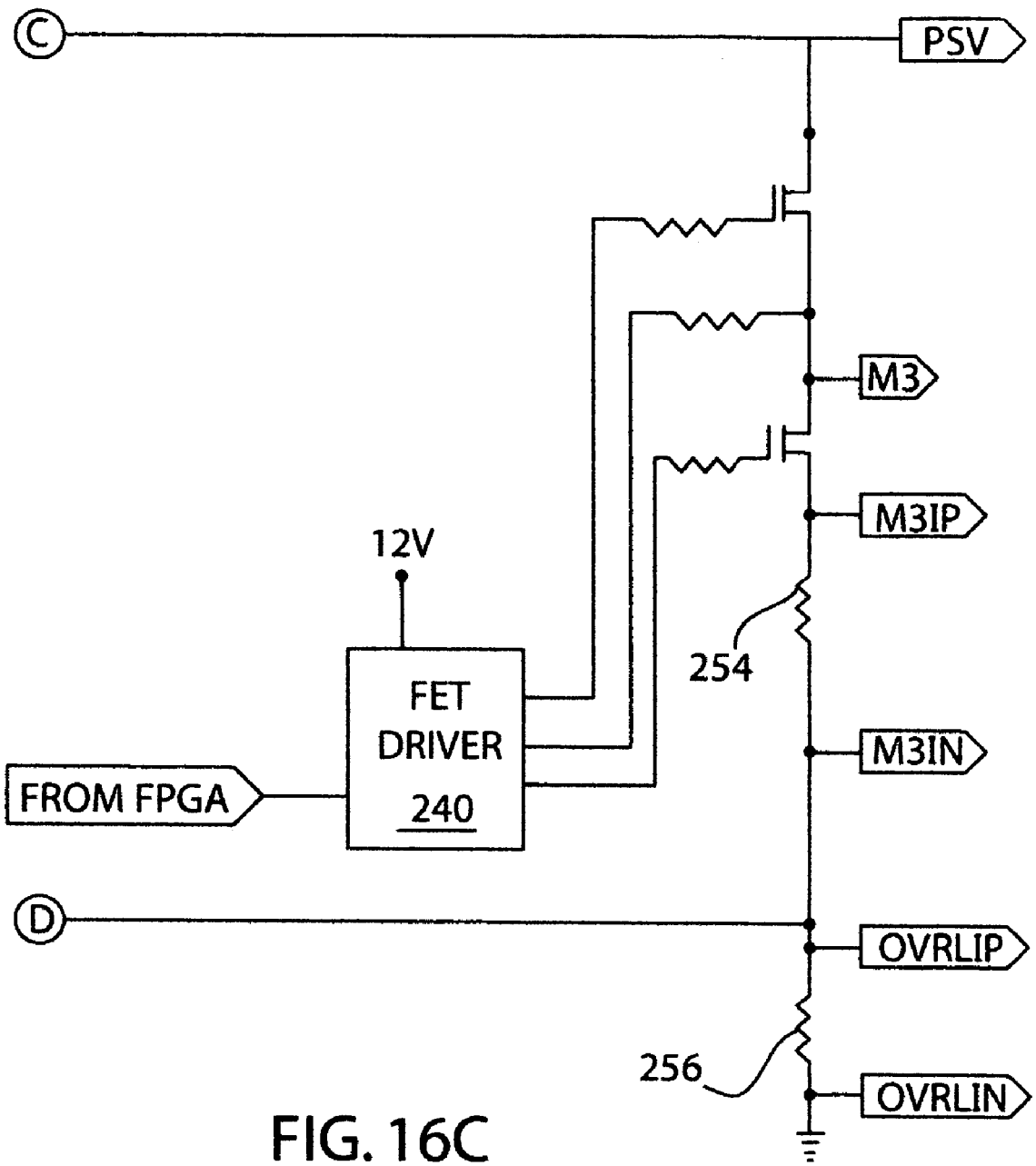

The basic structure of an H bridge 212 is shown in the block and schematic diagram formed by FIGS. 16A, 16B and 16C. By point of reference a stator 232 of a handpiece motor 36 to which the energization signals are applied is illustrated in FIG. 17. Stator 232 has three windings 234 that are tied to a common center point 236. The individual winding terminals that are tied to the 40 V power line, ground, or the BEMF analog circuit 214, are identified as M1, M2 and M3.

In FIG. 17, the depicted winding arrangement is of a wye-connected motor. It should be appreciated that system 10 of this invention can alos be used to regulate the actuation of delta-connected motors.

The 40 V power signal is received by a transient protection circuit 238 internal to the H bridge 212. Transient protection circuit 238 selectively inhibits the outputting of the 40 V signal to prevent any braking transient signals from one winding 234 from glitching over to a second winding. Internal to the transient protection circuit is a FET (not illustrated) that controls the outputting of the 40 V signal. This FET is gated by a control signal from the complementary FPGA 228 (connection not shown). The 40 V power signal is output from transient protection circuit 238 over a 40 V rail 240 internal to the H bridge.

For each winding 234, the H bridge 212 has two FETs 242 and 244, that, respectively, tie the winding terminal to the 40 V rail 240 or ground. In FIGS. 16A, 16B and 16C, the terminals tied to the winding terminals M1, M2 and M3, are identified as M1P, M2P and M3, respectively. FET 242 is tied between the 40 V rail 240 and the MxP terminal. FET 244 is tied between the MxP terminal and ground. Not shown are the reverse biased zener diodes connected across the sources and drains of FETs 242 and 244, one each per FET, for voltage protection.

Each pair of FETs 242 and 244 are controlled by a FET driver 246. Each FET driver 246, in response to control signals from the complementary FPGA 228, assert the gate signals to the complementary FETs 242 and 244. A base driver that can be used as the foundation of a FET driver is the IR218x Series High Voltage Gate Driver available from International Rectifier (Richardson Electronics) of LaFox, Ill. The control signal generated by the FET driver 246 to the gate of FET 242 is applied to the gate through a resistor 248. The FET driver monitors the voltage at the source of the FET 242 through a resistor 250. The control signal to tie a winding 234 to ground is applied to the gate of FET 244 through a resistor 252.

A resistor 254 is connected to the source of each FET 244. The opposed ends of each resistor 254 are tied together and connected to a common resistor 256. The opposed end of resistor 256 is tied to ground. The voltage across each resistor 254 is measured as being a signal representative across the motor winding 234 with which the resistor 254 is associated. This voltage is measured off the MxIP and MxIN terminals in FIGS. 16A, 16B and 16C. The voltage across resistor 256 is measured as being a signal representative of the total current drawn by the handpiece motor 36. This signal is measured across the OVRLIP and OVERLIN terminals of FIG. 16C.

One sub-circuit of the BEMF analog circuit 214 is now described by reference to FIG. 18. This particular sub-circuit is used to measure the voltage of the power supply. Specifically, the 40 V rail signal from H bridge 21 is applied to this circuit; the PSI terminals in FIGS. 16C and 18. The signal on this circuit is tied to ground through two series connected resistors 258 and 260. The divided 40 V signal at the junction of resistors 258 and 260 is buffered by a unity gain amplifier 262. The output signal for amplifier 262 is the PSV_SNS signal representative of the power supply voltage.

Figure 19:
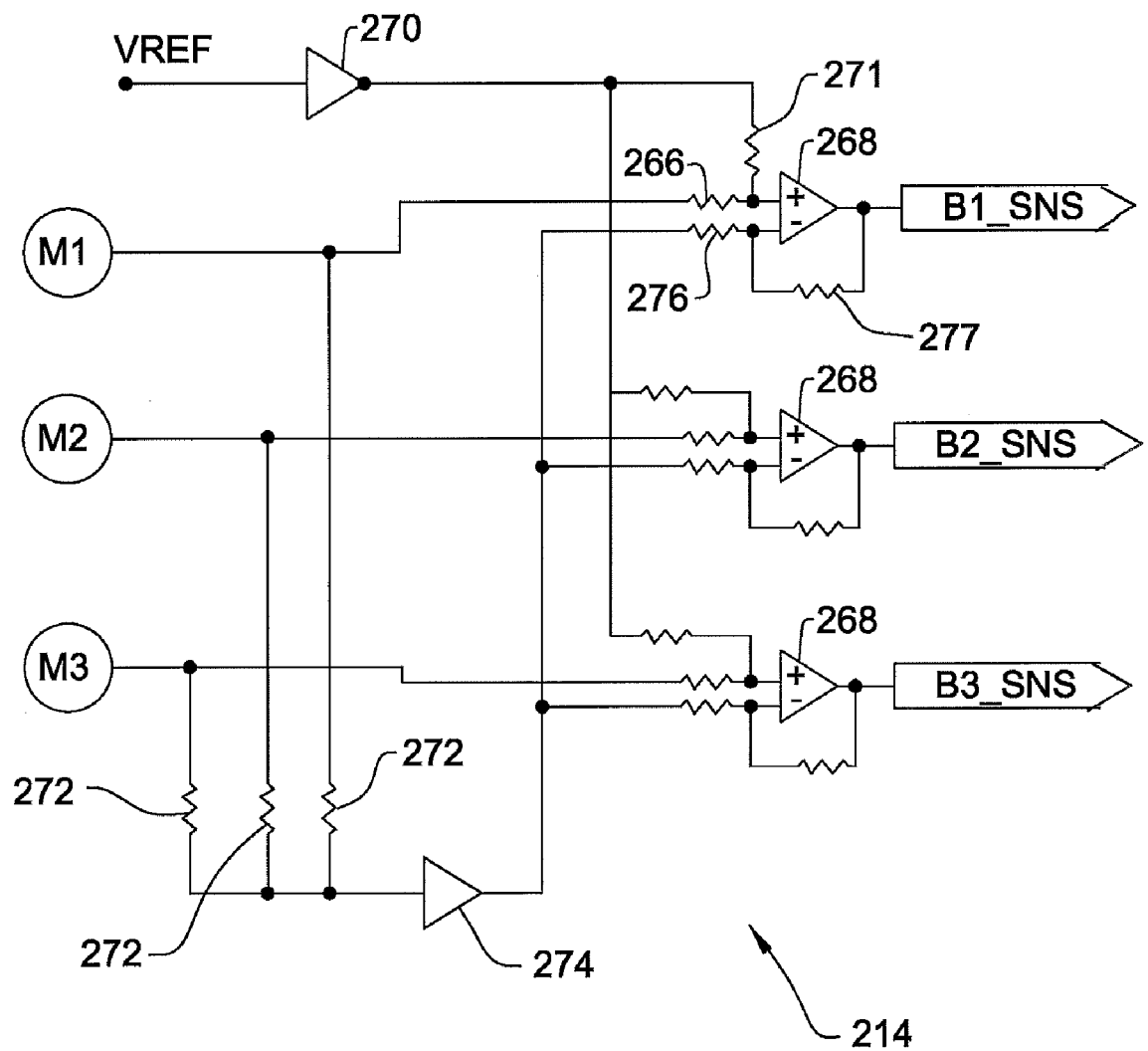
FIG. 19 is a block and partial schematic diagram of the circuit used to monitor the BEMF signals produced across the windings of the handpiece motor.

BEMF analog circuit 214 also includes the sub-circuit illustrated in FIG. 19. This is the actual sub-circuit that measures the BEMF signals developed across the motor windings 234 when they are not energized. In FIG. 19 the winding terminals are shown as being directly connected to the circuit. In actuality, each winding terminal M1, M2 and M3 is connected to a voltage divider and applied to a buffer amplifier. Thus the BEMF signals are preprocessed in manner similar to how the 40 V power signal is processed to form the PSV_SNS signal.

Each divided and buffered winding terminal signal is applied through a resistor 266 to the noninverting input of an amplifier 268. Also applied to the noninverting terminal of each amplifier 268 is a V_REF signal. This V_REF signal, prior to application to amplifiers 268 is buffered by a unity gain amplifier 270. The signal from amplifier 270 to amplifier 268 is applied through a resistor 272.

Each winding terminal is also connected to a separate resistor 272. The free ends of the resistors 272 are tied together and applied to a unity gain buffer amplifier 274. The output signal from amplifier 274 is applied to the inverting input of each amplifier 268. The signals to the separate amplifiers 268 are applied through separate resistors 276. A feedback resistor 277 is tied between the output and inverting input terminals of each amplifier 268. Thus, amplifier 268 is used to produce a recreated neutral voltage for the motor consisting of the sum of the Bx_SNS signals divided by three.

The output signal of each amplifier 268 is the measure of the BEMF signal at the winding terminal to which the amplifier is connected. These signals are represented as the B1_SNS, B2_SNS and B3_SNS signals in the drawings. It is understood that individually each of these signals is representative of the voltage at the associated winding terminal minus the recreated neutral voltage for the motor 36.

Figure 20:
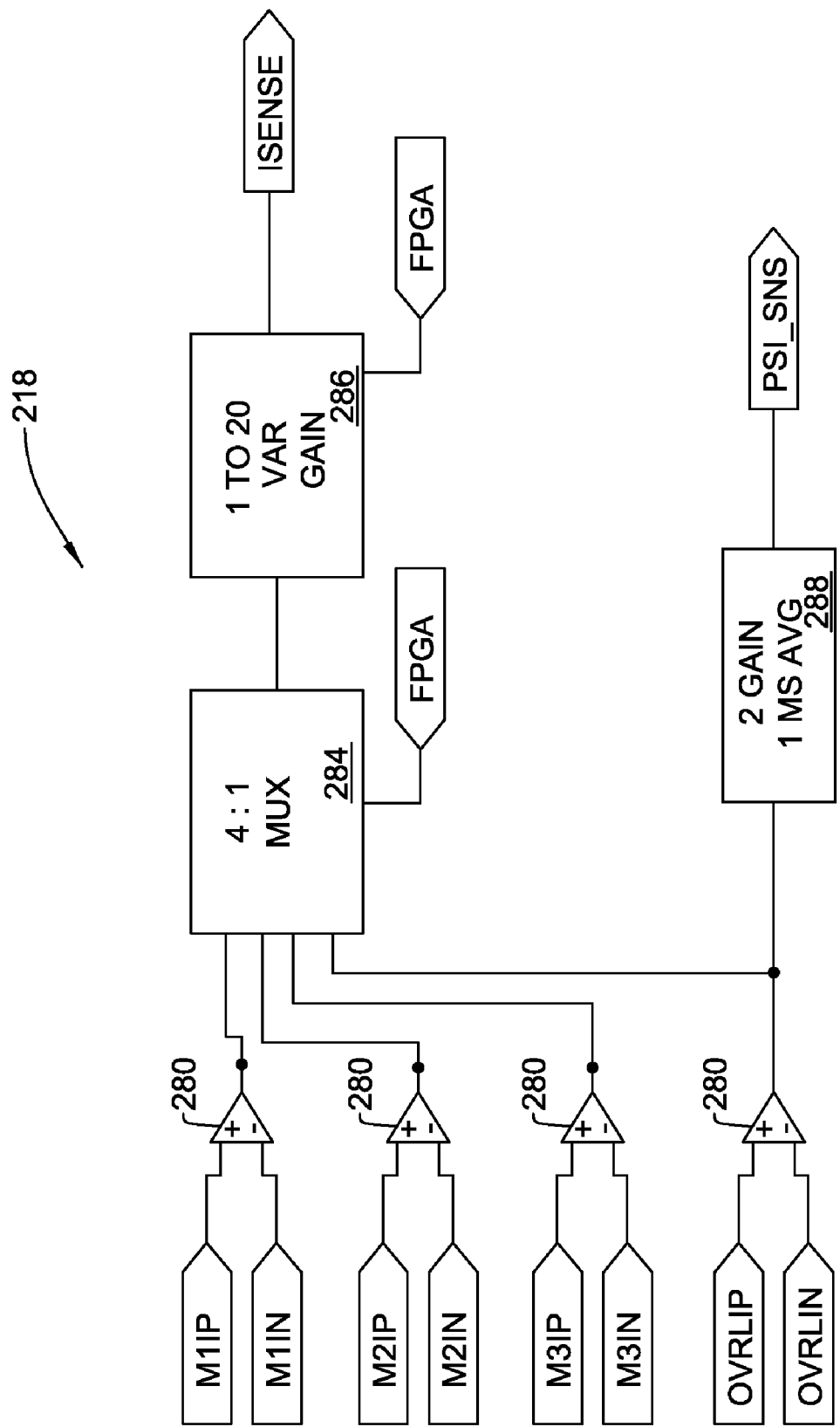
FIG. 20 is a block diagram of the circuit used to monitor the current drawn by the handpiece motor.

Referring to FIG. 20, a detailed description of the ISENSE analog circuit 218 is now provided. Each pair of MxIP and MxIN signals from the H bridge 212 are applied to, respectively, the noninverting and inverting inputs of separate differential amplifiers 280. The OVERLIP and OVERLIN signals are similarly applied, respectively, to the noninverting and inverting inputs of a differential amplifier 280. While not shown, it should be understood a buffered VREF signal is applied to each noninverting input of the amplifiers 280. Individual buffer amplifiers, (not illustrated) are used to apply the buffered VREF signal to the amplifiers 280. Each amplifier 280 serves as a ×10 gain circuit for the signal with which the amplifier is associated.

The signals from the individual amplifiers 280 are applied to a 4:1 multiplexer 284. Based on a control signal from the FPGA 228, multiplexer 284 selectively forwards one of the sensed current signals for further processing. The selected signal is forwarded from multiplexer 284 to a variable gain amplifier 286. In one version of the invention, amplifier 286 has a variable gain from 1 to 20. Amplifier 286 is a digital amplifier such that the gain can be adjusted in 256 steps. The command signals for establishing the gain of amplifier 286 come from the FPGA 228.

The output signal from amplifier 280 to which the OVERLIP and OVERLIN signals are applied is also applied to a gain and average circuit 288. This circuit multiplies the total motor current sensed circuit by 2. Circuit 288 also averages the signal over a select period, for example 1 millisecond. The output signal from gain and average circuit 288 is output as an average power drawn signal (PSI_SNS).

The BEMF analog to digital circuit 216 is now described by reference to FIG. 21. Circuit 216 includes a 5:1 multiplexer 292. Three input signals to multiplexer 292 are the three Bx_SNS BEMF signals from the BEMF analog circuit 214. A fourth input to multiplexer 292 is the PSV_SNS signal from buffer 262 representative of the power supply voltage. The remaining input to the multiplexer 292 is the PSI_SNS signal from gain and average circuit 288 representative of power supply current. A control signal from the FPGA 228 selects one of the five signals for further processing.

The signal selected by processing is output from multiplexer 292 to a high speed DC accurate buffer amplifier 294. Not illustrated is the feedback resistor tied between the output and inverting input of amplifier 294. Also not illustrated are the voltage limit diodes that are reverse biased tied to the output of amplifier 294. A first diode is tied between the amplifier 294 and the 5 Volt analog bus. A second diode is reverse bias tied between the output of amplifier 294 and ground.

The signal produced by amplifier 294 is applied to an analog-to-digital converter 296. The output signal from converter 296 is supplied to the FPGA 228.

The ISENSE analog to digital converter circuit 220 is illustrated in FIG. 22. The output signal from variable gain amplifier 286 is applied to a high speed buffer amplifier 298. Amplifier 298 and its supporting components, a feedback resistor and voltage limit diodes (components not illustrated) are similar to those attached to buffer amplifier 294. The output signal from buffer amplifier 298 is applied to an analog to digital converter 300. The output signal from converter 300 is applied to the FPGA 228.

Motor multiplexer 222 consists of six relay circuits 302, one of which is illustrated in FIG. 23. Each relay circuit receives a separate MxP signal. Three relay circuits 302 receive the M1P, M2P and M3P signals from one H bridge 212. The remaining relay circuits 302 receive the M1P, M2P and M3P signals from the second H bridge 212.

Each relay circuit 302 includes a first relay 304 and a second relay 306. The Mx signal is applied as input to relay 304. Relay 304 selectively applies the MxP signal to either one of the sockets 40, S3 in FIG. 23, or to relay 306. Relay 306 selectively applies the MxP signal to one of the remaining sockets 40, S1 or S2 in FIG. 23. The states of the relays 304 and 306 are regulated by control signals from the FPGA 228. These control signals are each applied to a FET 308. Each FET 308, controls the application of the 40 V signal to solenoid of the relay 304 or 306 with which the FET is associated. The 40 V signal is applied to each FET 308 through a resistor 309. The signal present at the drain of each FET 308 is applied to ground through two series connected resistors 310 and 312. The signals present at the resistor 310 and 312 junctions are applied back to the FPGA 228. The FPGA 228 uses these returned signals as status signals to verify the state of the relay circuits it should also be appreciated that only a pair of control signals from each FPGA 228 control the setting of the three relay circuits 302 that complement the specific FPGA. Similarly, only two status signals for the three relay circuits are returned to the FPGA 228.

Figure 24:
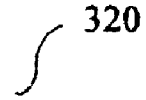
FIG. 24 depicts the records contained in the power driver assignment table.

Display controller 64 and motor processor 224 exchange signals over SPI bus 88. As part of the process of maintaining overall control of system 30 of this invention, display controller 64 maintains a power driver assignment table 320, FIG. 24. Internal to table 32 are two power driver assignment fields 322. Each power drive assignment field 322 is associated with a separate one power driver and sense circuits 210. The data in each field 322 indicates whether or not the associated power driver and sense circuit 210 is being used to energize a particular handpiece 34.

When the surgeon actuates one of the handpieces, display controller reads the data in the power driver assignment fields 322. Base on these data, display controller determines whether or not one of the power driver and sense circuits 210 is available to supply the energization signals to the handpiece 34. If one of the circuits 210 is available, the circuit is assigned to handpiece. Display controller 64 rewrites the data into the power driver assignment table 320 to indicate to which handpiece the newly assigned power driver circuit 210 has been assigned.

Display controller 64 also sends an initialization packet to motor processor 224. This packet contains data identifying which of the power driver and sense circuits 210 has been assigned to a handpiece 34. The types of data contained in the initialization data packet are discussed below.

Figure 32A:
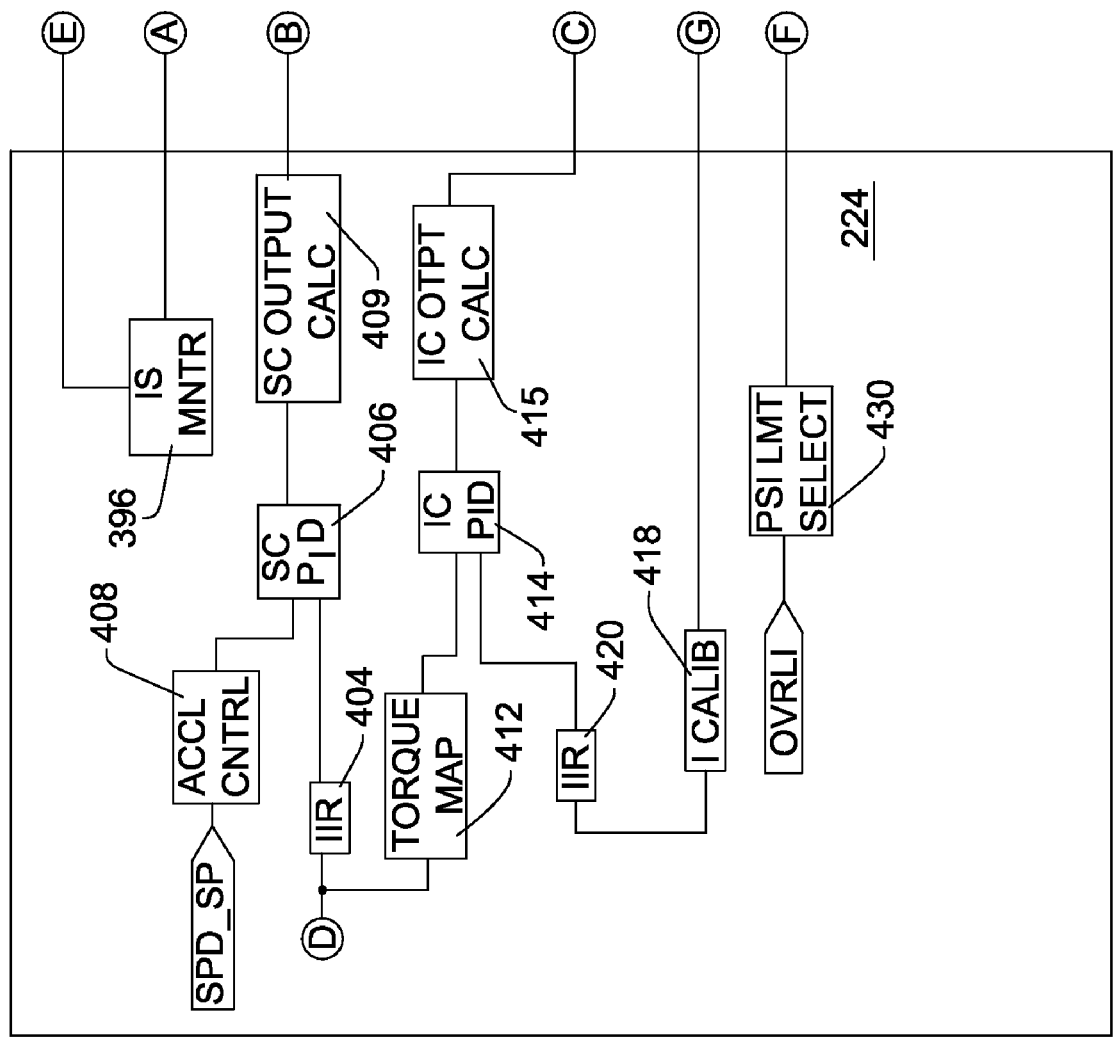
FIGS. 32A and 32B collectively represent the processes executed by the motor processor and a single field programmable gate array of the motor control to regulate the energization of a handpiece.
Figure 32B:
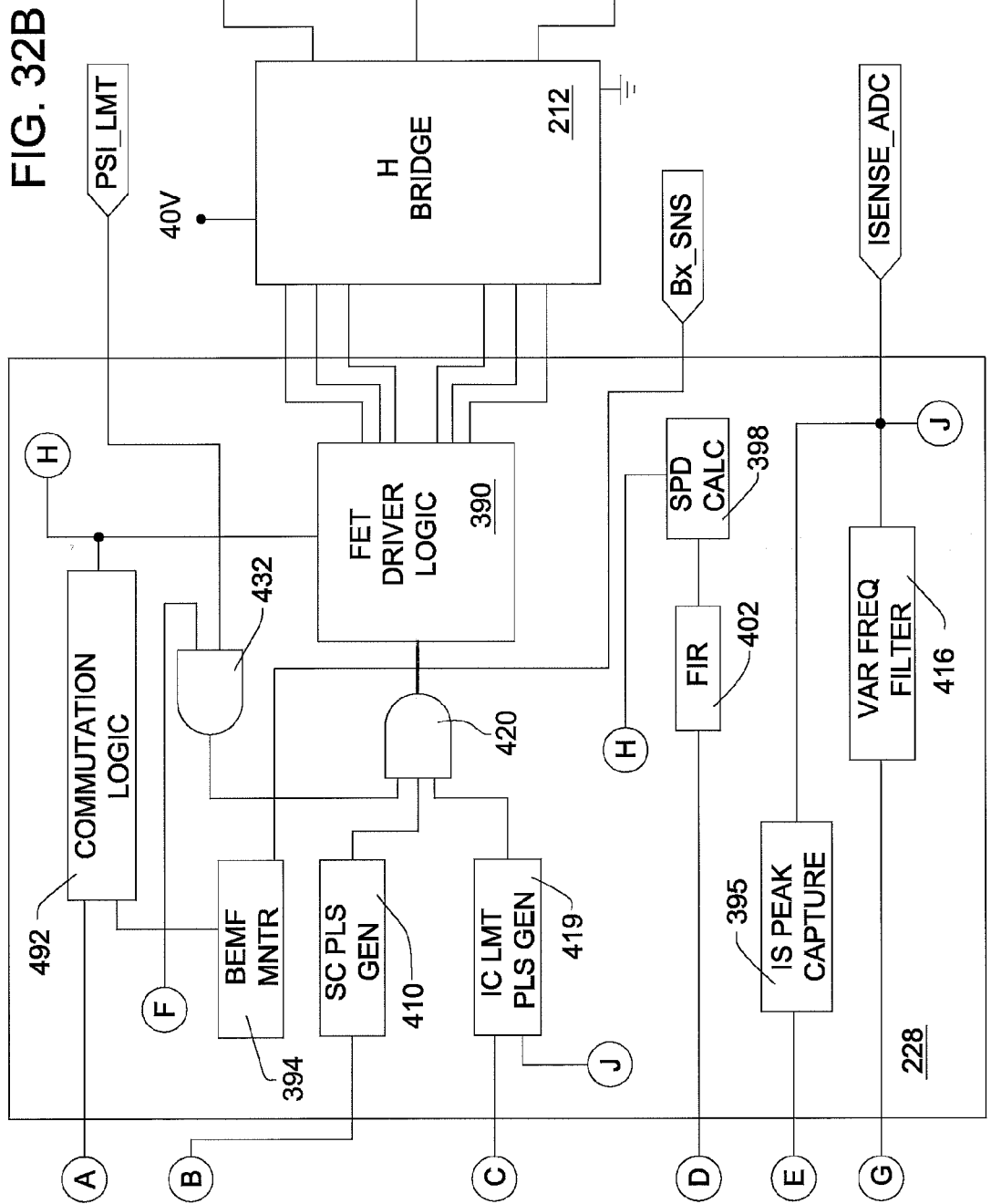

FIGS. 32A and 32B collectively illustrate the control processes executed by motor controller 224 and an FPGA 228 to regulate the application of energization signals to the windings 234 of an attached handpiece motor 36. FIG. 32A illustrates the processes run of the motor processor 224. The processes run on the FPGA 228 are illustrated in FIG. 32B. Generally it should be understood that the goal of these processes is to generate six (6) driver signals, one to each of the FETs 242 and 244 internal to H bridge 212. The turning on and off of FETs 242 and 244 is what causes current flow through the selected pair of windings at the selected chop rate.

One process module internal to the FPGA 228 is a FET driver logic module 390. Module 390 is the module internal to the FPGA that generates the signals to gate FETs 242 and 244. In FIG. 32B this is represented by the six conductors that extend from the FET driver logic module 390 to the H bridge. In order to minimize confusion, subsequent discussed connections are illustrated with only a single line conductor even when multiple conductors are present. Also, it should be recognized that many of the subsequent discussed connections are within the same integrated circuit component.

The input signals to the FET driver logic module 390 are the instruction signals used to regulate the commutation of the windings and the driving of the windings. The commutation instruction signals inform FET driver logic module 390 across which pair of windings the energization signals should be applied. The drive signals inform FET driver logic module 390 of what the PWM rate and on duty cycle should be for the energization signals. Based on these instructions, module 390 generates the gate signals to turn FETs 242 and 244 off in an appropriate sequence.

The commutation instruction signals are generated by a commutation logic module 392 also internal to FPGA 228. Module 392, receives as input signals indicating the angular position of the motor rotor. Based on these signals, commutation logic module 392 generates the commutation instruction signals to FET driver logic module 390.

In the system of this invention, there are two alternative processes by which motor rotor position is determined. Internal to the FPGA 228 is a BEMF monitor module 394. Module 394 receives as input the digitzed BEMF signals from the BEMF analog to digital converter 216. In FIG. 32B, these signals are represented as Bx_SNS signals. Based on these signals, the BEMF module 394 determines rotor position. Module 394 provides this information to the commutation and logic module 392.

As discussed below, when the handpiece motor 36 is operating at a low speeds, the BEMF signals cannot be used to determine rotor position. Thus, when the handpiece 34 is in this state, control console uses the second method of determining rotor position inductance sensing. Inductance sensing is performed by an inductance sensing (IS) monitor module 396 internal to the motor processor 224. Generally, it should be understood that in inductance sensing, current through the windings 234 is measured to determine rotor position. The inputs signals into the IS monitor module 396 are measurements of the captured peaks of the measured current flows through the individual windings 234. These peaks are captured by a IS peak capture module 395 located in the FPGA 228. The input signals into module 395 are the digitized current measurement signals from the individual windings. It should be appreciated that, in inductance sensing mode, the current through resistor 256 is the current that is measured.

These currents are proportional to the voltages across resistors 254 of the H bridge. Digitzed representations of these signals are passed from the ISENSE analog to digital circuit 220 are passed from the FPGA 228 to the motor processor 224, connection not shown. A discussion of how inductance sensing processes are used to determine rotor position is set forth below. The rotor position determinations made by inductance sensing monitor module 396 are provided to the commutation logic module 392.

It should further be appreciated that motor controller 224 determines when the commutation logic module 392 should rely on BEMF sensed determinations of rotor position and when the module 392 should rely on the inductance sensed determinations. Motor processor 224 makes this determination based on the actual speed of the handpiece motor and speed cutoff data from the handpiece NOVRAM 72. This cutoff data, the field in which it is stored not shown, indicates below what speed inductance sensed rotor position determinations are used to regulate commutation. This cut off speed is supplied to the motor processor 224 as part of the initialization packet. Thus while the input connections are not show, it should be further understood that inductance sensing monitor module 396 also receives an indication of motor speed and the cutoff speed to perform the required comparison.

It should further be understood that inductance sensing monitor module 396 also communicates with BEMF module 394, connection not shown Specifically, inductance sensing monitor module 396 provides the initial start logic data to the BEMF module 394 that module 394 needs to perform BEMF monitoring of rotor position.

Three basic input variables are used to cause the windings to be driven. One input is based on the difference between the actual and user-selected speed for the handpiece motor. A second input is based on the current drawn by the motor 36. The third input is based on the overall power that is, at any given instant, being consumed by the system 10.

The digitized BEMF signals, the Bx_SNS signals in FIG. 32B are what is used by the FPGA 228 to determine raw speed of the handpiece motor 36. Specifically, internal to the FPGA 228 is a speed calculator module 398. Speed calculator module 398, receives the output commutation instruction signals from the commutation logic module 392, connection H in FIG. 32B. Based on the times between the commutations as designated by these signals, speed calculator module 398 generates a digital representation of rotor speed. This speed value is filterd by an FIR filter 402 internal to the FPGA. The coefficients for this filter from the handpiece NOVRAM 72 are contained in the initialization packet. (It should likewise be appreciated, the filter coefficients for all filters in the DSP 224 and FPGA 228 come from the NOVRAM 72 in the initialization packet.

The filtered speed signal is forwarded from the FPGA 228 to an IIR filter 404. The filtered signal IIR filter 404 is applied as one input variable to a speed control (SC) proportional integral derivative (PID) algorithm module 406.

The second variable into the SC PID module 406 is a user speed set-point signal. This signal is generally a digital representation of the user selected speed for the handpiece. This signal is provided by display controller 64 in both the initialization packet and in speed set-point packets. These speed set-point packets are repeatedly sent by the display controller 86 to motor processor 224 as long as the handpiece remains actuated. Each speed set-point packet contains data identifying the handpiece 34 with which the packet is associated and data indicating the user-set speed for the handpiece 34. These latter data are determined by the display controller by reference to the input device the surgeon actuates to change motor speed. While a handpiece remains actuated, display controller 64 typically sends a speed set-point packet once every 10 milliseconds.

Prior to the speed set-point signal being received by the SC PID module 406, the signal may be processed by an acceleration control module 408. This is because over time, the speed set-point signal will change as a result of the surgeon speeding up, slowing down, or braking the handpiece motor 36. Depending of the rate of change of the actual speed set-point signal, acceleration control module 408 adjusts the rate at which the set-point signal applied to the SC PID module 406 actually changes. This is done to minimize any jerking or other uneven operation of the handpiece motor 34 that may occur as a result of rapid acceleration, deceleration or braking.

It should be recognized that the parameters the acceleration control module uses to modify the rate of change of the speed set-point signal come from the handpiece NOVRAM 72 in the initialization packet.

The SC PID module 406, based on the difference between the actual (filtered) motor speed and the speed indicated by the set-point signal determines an SC PID output signal. The algorithm by which this signal is generated is made is known in the art.

While there are two constantly changing inputs into the SC PID module 406, it should be appreciated that there are other variables into the algorithm. These variables include, proportional gain, integral gain derivative, gain and derivative time constant, output max and output min. These variables, which are essentially constant, are supplied from the handpiece NOVRAM 72 by the initialization packet. For some motors, different sets of these variables are employed for speed control purposes at different speed ranges. The multiple sets of variables are supplied in the initialization packet. Based on the current speed range in which the handpiece motor 36 is operating, motor processor 224 loads the appropriate set of variables into the SC PID module 406.

The above mentioned constant-over-speed range variables are also supplied to a current control (IC) PID module 414. It should be appreciated that the set of variables applied to the SC PID and IC PID modules 406 and 414, respectively, are different.

The SC PID output signal from module 406 is applied to an SC output calculation module 408. A second input into module 408 is a motor PWM frequency. This variable is from the handpiece NOVRAM 72 and is supplied in the initialization packet. Based on these inputs, SC output calculation module 409 determines two values, the PWM period and the PWM on time for the drive signal.

Output signals representative of the values produced by the SC output calculation module are forwarded to a SC pulse generator 410 internal to the FPGA 228. The SC pulse generator 410, based on the inputs from module 409 produces a train of speed control-based PWM drive pulses.

The current based drive signals are based on both a current set-point for the handpiece motor 36 and the actual current drawn by the motor. A torque map module 412 produces the current set-point value. The three variables from which the current set-point is determined are, the speed of the motor, a torque map and a constant. Torque map module 412 receives the filtered speed signal from the FPGA FIR 402. The torque map is a relationship specific to the motor of the torque the motor can develop at a specific speed. The constant converts the speed-based torque into a current set-point. The data for the torque may and the constant are from the NOVRAM 72 and contained in the initialization packet.

Thus, for a given speed, based on the torque map, module 412 determines the torque the motor should developed. Based on this determination and the constant, module 412 determines the current the motor should draw. Torque map module 412 supplies data representative of this current set-point to the IC PID 414 algorithm module.

The second continually varying input into the IC PID module 414 is the actual current drawn by the motor. The current measurement supplied to module 414 is based on the interleaved individual winding current measurements from across resistors 254 of the H bridge 212, the MxI signals in FIG. 32B. These signals are supplied to a two stage variable frequency filter 416 in the FPGA 228. Filter 228 removes the high frequency ripple in this current signal to commutation switching.

The filtered current signal from filter 228 is applied to a current calibration module 418 internal to the motor processor 224. Current calibration module 418 calibrates the current for subsequent processing. A variable module 418 employs to determine the extent the current drawn signal needs to be calibrated is the value indicating the extent the analog version of the current signal was amplified by variable gain amplifier 286. This value, as well as the setting for amplifier 286 are from the handpiece NOVRAM 72 and contained in the initialization packet.

The calibrated current reading is filtered by an IIR 420 also in the motor processor 224. The filtered sensed current is applied to the IC PID module 414 as the second variable.

Based on the current set point and the filtered and calibrated measurement of actual current, the IC PID module produces a midpoint current value. The midpoint current value is forwarded to a current control output calculation module 415. From the initialization packet, module 415 previously received current range window data. These data indicate a range between which the motor current should oscillate. Based on these window range data and the midpoint current value, current control output calculation module 415 produces ILIMITH (high) and ILIMITL (low) current limits.

It should be appreciated that the midpoint current value is between these current limits. The range between the limits is based on the range data in the initialization packet.

The motor processor 224 provides the ILIMITH and ILIMITL values to a current control limit pulse generator 419 internal to the FPGA. Generator 419 receives as another input a measure of the actual motor current. In actuality the interleaved digitized versions of the three winding currents, the digitized MxI current signals are applied to generator 419. Based on the ILIMITx values and the measured current, current control limit pulse generator 419, based on a bang-bang process, selectively clocks out current control drive pulses.

The speed control-based PWM drive pulses from the SC pulse generator 410 and the current control drive pulses from the current control limit pulse generator 419 are two of the signals used to control the generation of driving of the windings 234. The third input signal is a power supply limit (PSI_LMT) signal. As discussed below, this signal is asserted when the components of system 10 consume more power than the console power supply 90 can provide.

These three signals are applied to an AND logic module 422 internal to the FPGA 228. The output from module 422 is applied to FET driver logic module 390 as the signal to drive the windings 234. AND logic module 422 is configured to assert the signal to drive the windings 234 only when the speed control-based PWM drive pulses and the current control drive pulses simultaneous indicate the windings are to be driven and the power limit exceeded signal is not asserted.

It should be recognized that a feature of the above assembly is that it provides for precise torque control of the operation of a handpiece 34. Specifically, by entering the appropriate commands, display controller 64 is directed to present on display 42 torque control setting images. By pressing the touch screen buttons associated with these images, the surgeon established the maximum torque the handpiece motor is to develop. This is useful because for certain procedures, such as the driving in of a implant into tissue, only a select maximum amount of torque should be applied. Once the surgeon establishes this torque limit, data regarding its value is provided by display controller 64 to motor controller 224 in the initialization packet. Based on these data, motor processor 224 configures the torque map module 412 to ensure that the module never generates a signal indicating that the handpiece motor 36 should produce more torque than the defined maximum amount.

Figure 33:
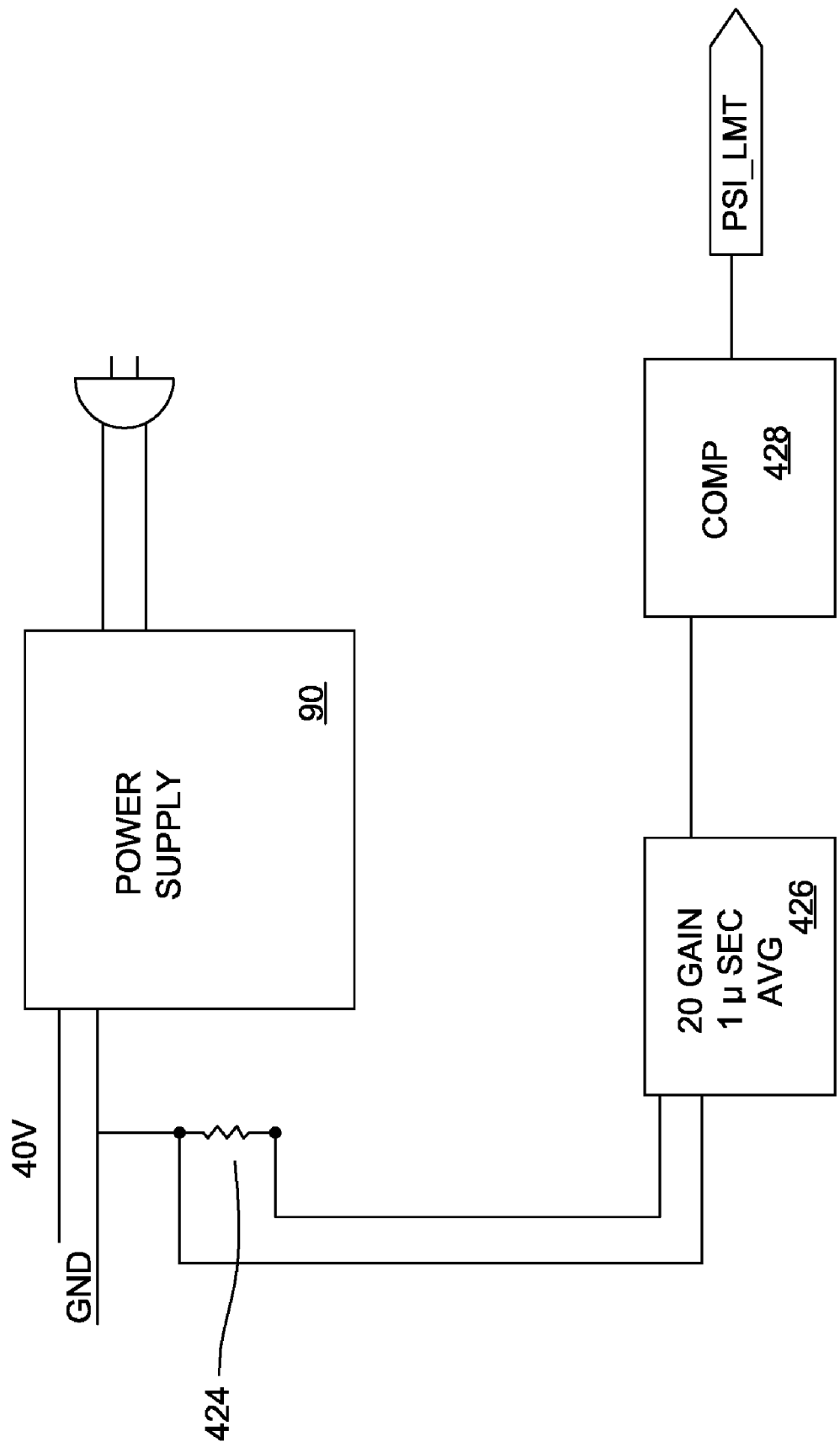
FIG. 33 is a block and partial schematic drawing of the circuit that selectively asserts the power supply limit signal.

An understanding of when and how the power supply limit signal is asserted can be obtained by initial reference to FIG. 33. Initially it should be understood that the reason a means for power limiting is provided is that there may be times when surgeons may attempt to simultaneously drive two instruments that collectively consume more power than control console 32 can provide. This is because amount of power any power supply can provide is invariably limited. By way of example, it should be understood that in some versions of the invention it is anticipated power supply 90 provides up to 400 Watts of power. For reasons of size and to minimize the amount of heat emitted by the control console 32, it is often considered reasonable design consideration to so limit the amount of power the control console can provide. Moreover, there are seldom instances when both handpieces being simultaneously driven by the control console will need more than 400 Watts of power. Therefore, it should be appreciated that is not an efficient use of resources to provide a power supply that could supply more power.

However, there may occasionally be instances when two high-power consuming handpieces 34 are simultaneously connected to and energized by the control console 32. The power supply limit circuit of system 10 of this invention allows both handpieces to be so actuated.

As seen by reference to FIG. 33, the power supply limit circuit includes a resistor 424 connected to the ground out of the power supply across which the current out of the power supply 40 is measured. The voltage across resistor 424 is gain and average circuit 426, multipled and averaged. In one version of the invention, this current drawn signal is multipled by 20 and averaged over 1 microsecond.

The multiplied and averaged power supply current signal from circuit 426 is applied to a comparator 428. The second input to comparator 428 is a reference signal, not shown representative of the maximum current the power should draw. The power is provided to the handpieces in the form of a 40 volt potential. Therefore, the maximum current the power supply should draw to ensure that it does not consume more than 400 Watts is 10 Amps. In actuality, the power supply 90 is capable of consuming up to 500 Watts, the additional however is used by the internal console components such as pump motor 60. Performing the power limit monitoring at a level less than power supply's actual power limit, essentially eliminates the likelihood the power supply could consume so much power there could be component failure.

Thus, comparator 428 continual monitors the adjusted power supply current to determine whether or not the power supply is consuming too much current. If this condition occurs, comparator 428 asserts the PSI_LMT signal.

The PSI_LMT signal is applied to both FPGAs 228. As part of the overall process of regulating the energization of the handpiece motors 36, motor processor 224 continually determines which motor, in view of the power limit being exceeded, should temporarily be deactuated. This determination is made by a power supply current (PSI) limit select module 430 internal to the motor processor 224. The inputs into module 430 are values of the current presently being drawn by each handpiece motor 36. Specifically these are current drawn measurements through the H bridge resistors 256. In FIG. 32A this is depicted by a single OVERLI signal directly into module 430. In actuality it is understood that digitized forms of these motor current signals are forwarded from both FPGAs 228 to the PSI limit select module 430. By comparing these signals, module 430 determines which of the two actuated handpiece motors 36 at any given instant is drawing more current, consuming more power. The PSI limit module 430 selects this handpiece motor 36 for potential power limited necessitated deactivation.

Specifically, PSI limit module 430 asserts a power limit enable signal to an AND logic module 432 internal to the FPGA 228 associated with the selected handpiece motor 36. The PSI_LMT signal, when asserted, is simultaneously received by the AND logic modules 432 of both FPGAs 228. Only the module 432 to which power limit enable signal has been asserted forwards the PSI_LMT signal. Specifically, this signal is forwarded to AND logic module 422. As discussed above, when AND logic module 422 receives the PSI_LMT signal, module 422 inhibits the assertion of the drive signals to FET driver logic 390.

Thus the assertion of the PSI_LMT signal causes the enabled FPGA 228 to temporarily stop asserting drive signals. This stops the application of energization signal across the windings of the motor 36. Thus the motor is forced to temporarily coast. This does prevent the power supply 90 from consuming more than the amount of power it is designed to consume.

As discussed above, at normal operating speeds, the FPGA 228 associated with the driver power driver and sense circuit 210, regulates the commutation switching of the motor windings 234 by monitoring the BEMF signals generated across the unenergized motor winding 234. However, at low speeds, speeds 10% or below of the maximum operating speed of the handpiece motor 36, and for some handpieces, speeds 5% or below the BEMF signal across a winding drops to a level at which it cannot be detected.

Figure 27:
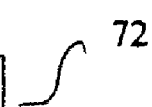
FIG. 27 depicts how a handpiece NOVRAM of the system of this invention includes gain and offset data to facilitate the inductive signal sensing of the handpiece rotor.

When this event occurs, motor controller 86 employs inductance sensing to determine the position of the motor rotor. More particularly, as seen in FIG. 27 internal to handpiece NOVRAM 72 there is a BEMF/IS set point field 339. Field 339 contains data that indicates the speed above which motor controller 86 should employ BEMF sensing to determine rotor position. At speeds at or below the speed set forth in field 339, motor controller 86 employs the below-described inductive sensing process to determine rotor position. The speed level in the BEMF/IS set point field is supplied by display controller 64 to the motor processor 224 in the initialization packet. Based on the data indicating motor speed and the value from field 339, motor processor 224 selectively uses BEMF sensing or inductive sensing to regulate the energization of the handpiece motor 36.

The motor controller 86 starts the inductance sensing process by measuring the inductance across the windings in each of the six motor phases. This is performed by first negating the application of energization signals to the windings 234 as represented by time period 336 in the plot of FIG. 25.

Figure 25:
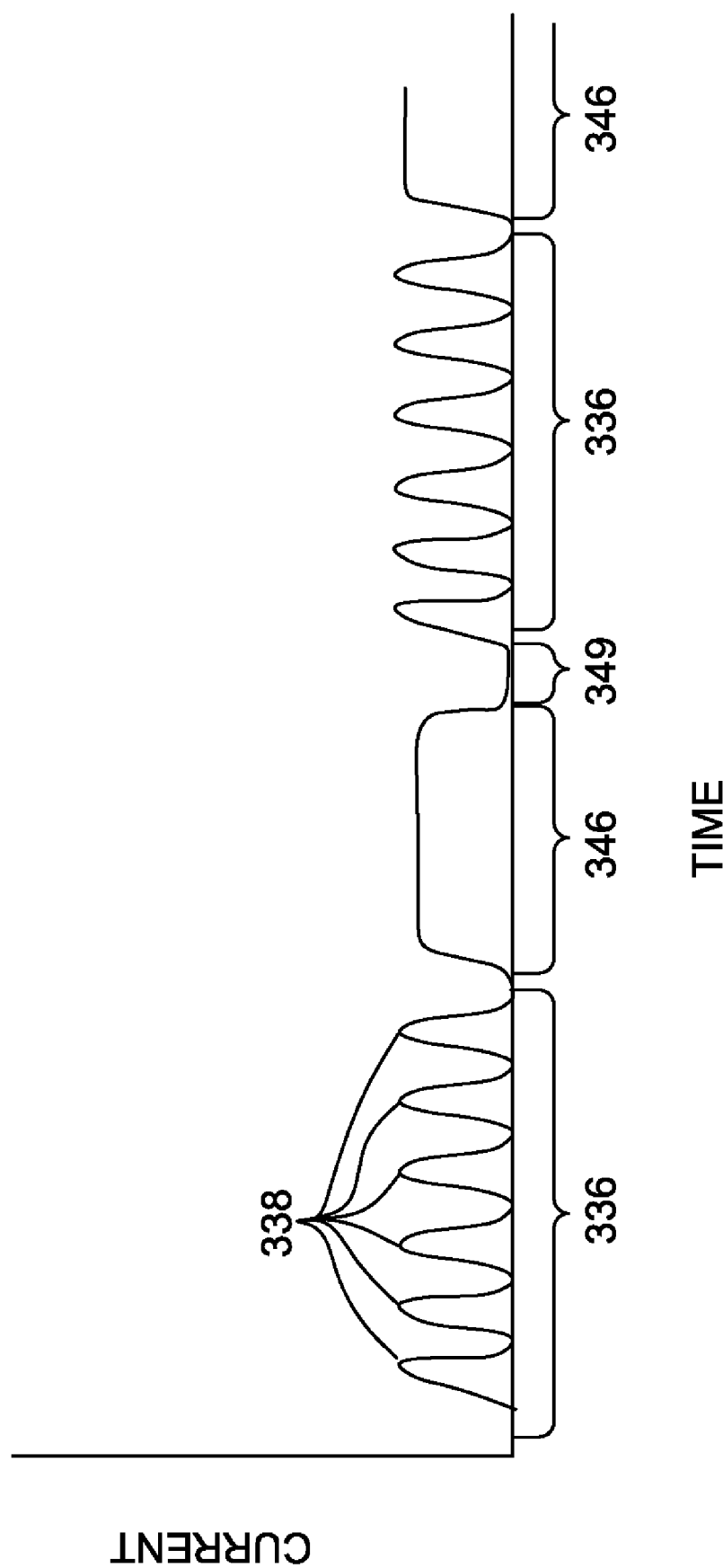
FIG. 25 is a graph of current over time depicting the measured current of a handpiece motor when the system is an inductance sensing mode for the motor.

Then, during time period 336, short voltage pulses are applied across each motor winding 234. In order to measure inductance in a first phase, one of the windings is tied to the 40 V rail 240 of the H bridge 212, the remaining two windings are tied to ground. The current developed by the winding connected to the 40 V rail 240 is then measured. To measure inductance in a second phase opposite the first phase, the two windings the power connections of the windings are reversed. Thus, the two windings just tied to ground are connected to the 40 V rail 240; the winding 234 attached to the rail is tied to ground. Current through the ground tied winding is then measured. These measurements are made for all three windings 234. Thus as depicted in FIG. 25, there are six measured current pulses 338 from the motor 36.

In theory, for any given position of the motor rotor, the measured current for one of the motor phases should be higher than measured current for the remaining five phase measurements. This is because the position of the rotor magnets affects the inductance across the windings and therefore, the current through windings.

Figure 26:
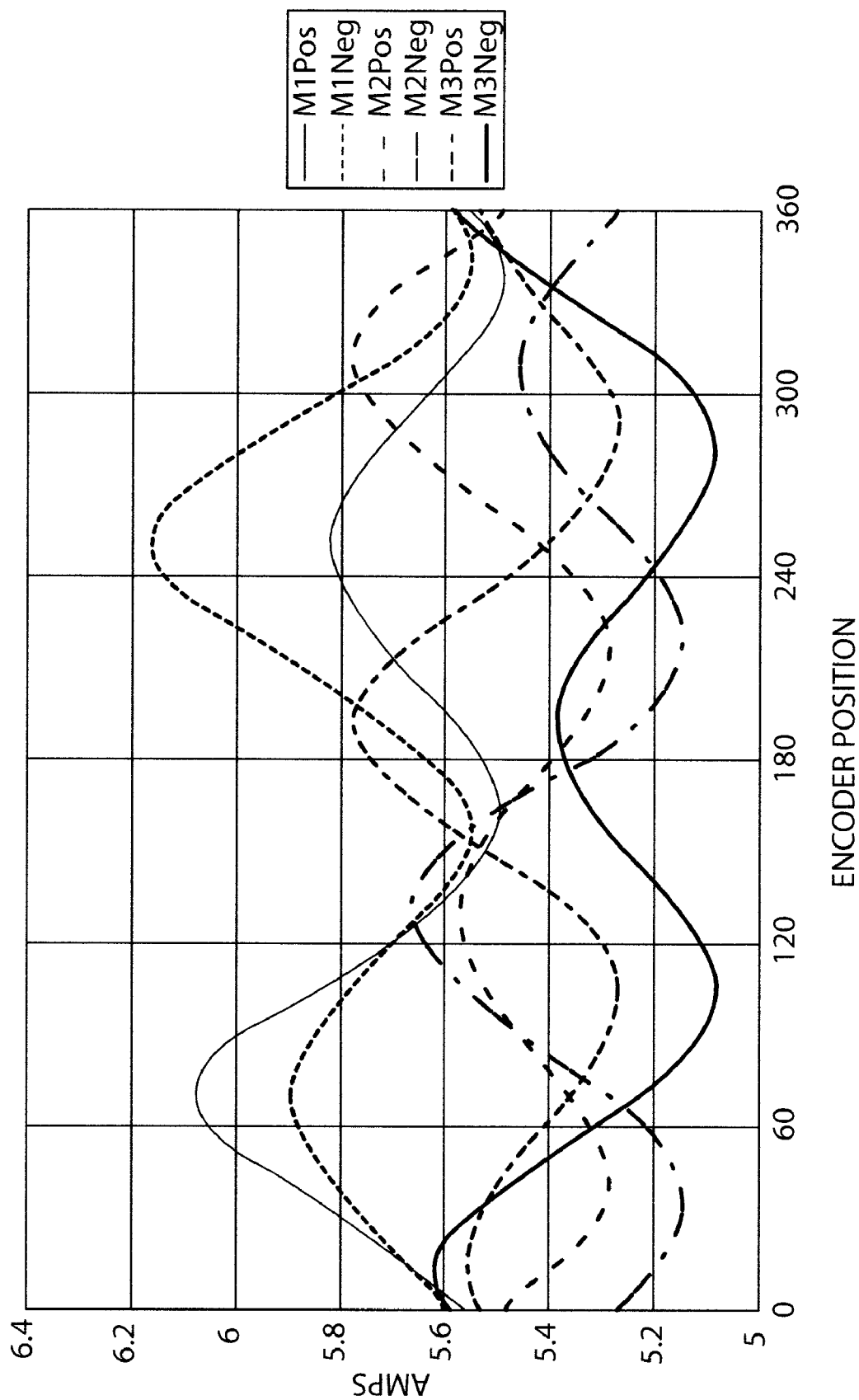
FIG. 26 is a graph of the relationship of measured current to motor rotor position for a surgical handpiece.

However, as indicated by reference to the graph of FIG. 26, in actuality, it has been found that for the DC motors of surgical handpieces 34, there is a poor correlation of measured inductance to rotor position. It is believed this poor correlation is due to the fact that the handpieces 34 integral with system 30 of this invention have motors 36 with relatively small rotors. In particular the rotors typically are 0.5 inches or less in diameter. Still other of the motor rotors have diameters of 0.25 inches or less. Due to the relatively small size of the magnets integral with these rotors, the magnets do not change the inductance of the adjacent motor windings 234 to the degree at which inductance changes alone can be used to determine rotor position.

Thus, in system 30 of this motor processor 224 applies gain and offset values to the measured motor phase currents. These gain and offset values come from data fields 340 and 342, illustrated in FIG. 27, within handpiece NOVRAM 72. Specifically, for each rotor position, NOVRAM 72 contains data in field 340 that includes the coefficient for multiplying the measured current, to produce the gain. Data in each field 342 contains a constant that is applied to the multiplied gain, the offset. These data, as well as the data in the BEMF/IS speed set point field 339 are forwarded from display controller 64 to motor processor 224 as part of the initialization packet.

It should be understood that for each type of motor 36, the gain and offset values for fields 340 and 342, respectively, are developed by empirical analysis of the operation of the motor.

Figure 28:
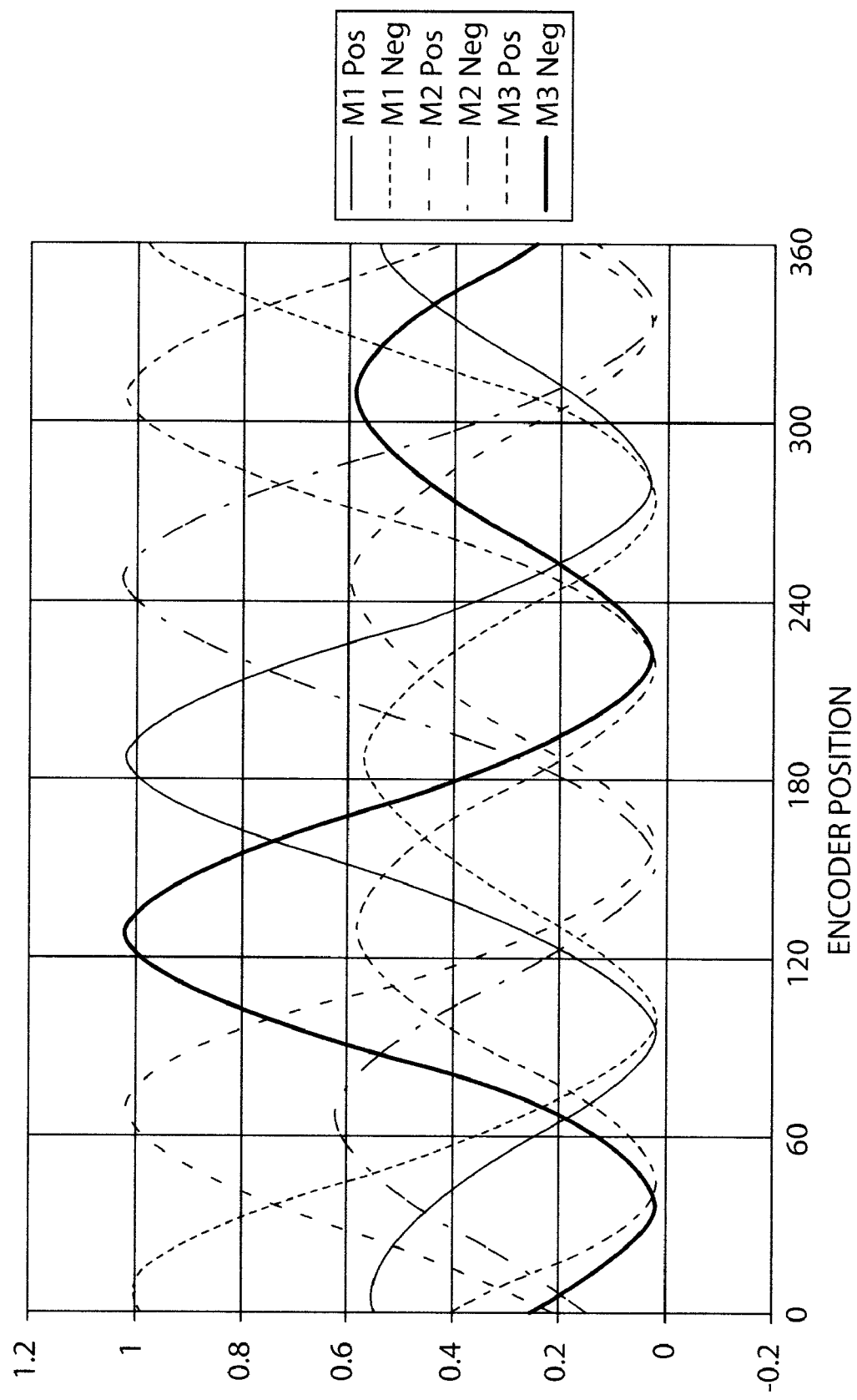
FIG. 28 is a graph of calibrated measured rotor current to motor rotor position when inductive sensing is performed.

Based on these retrieved gain and offset data, motor processor 224 is able to produced a calibrated, normalized current measurement for each current value. As seen by reference to FIG. 28, these calibrated normalized values result in a plot wherein for each rotor position a single one of the current values is higher than the other current values.

Thus, based on these calibrated and normalized measurements of winding inductance, motor processor 228 is able to determine the position of the motor rotor. Based on this determination, motor processor 228 is able to determine through which windings 234 current should next be applied. This is represented in FIG. 25 by period 346 an energization signal is applied to across the appropriate two of the motor windings 234. It will be noted also from this figure that a quiescent period 349 that proceeds period 336 so the current measurements can made. Collectively, periods 336 and 349 are approximately 10% of the size of period 346 in which a signal is applied to a single winding pair to actuate the motor. Generally the combined period for a single cycle of periods 336, 346 and 350 is 1 millisecond.

It should be recognized that this use of inductance measurement sensing to monitor rotor position and regulate the energization of windings can be used in situations other than when the handpiece motor 36 is operating in a low speed state. This inductance measurement sensing can be used to regulate winding energization even when the motor is stopped, a 0 RPM speed. Thus, inductance measurement sensing can be used to regulate motor start up when the handpiece is initially actuated. Inductance measurement sensing can also be used to regulate motor actuation when as a result of the motor developing an amount of torque that approaches or equals the maximum torque it can develop the motor rotor slows to a very low speed or even stops.

Figure 29:
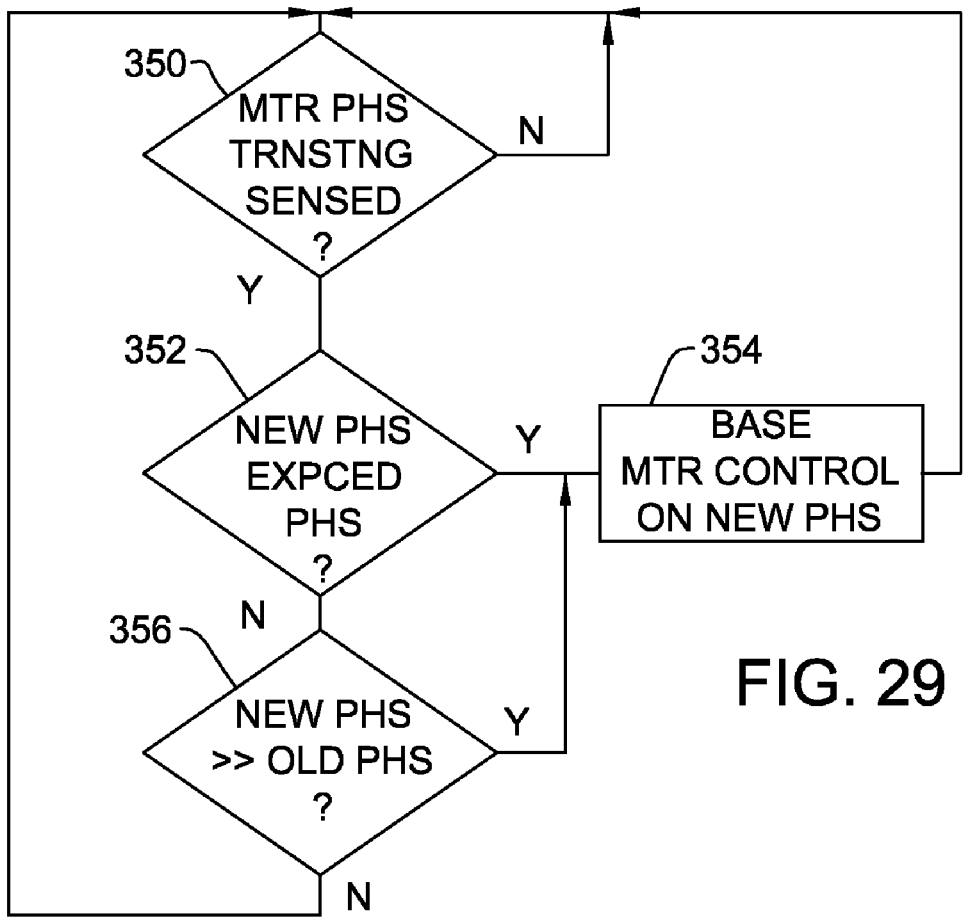
FIG. 29 is flow chart of the process steps executed by the motor controller during inductance sensing mode to determine whether or not, based on a transition to particular motor pole state, the motor rotor should be have considered to have shifted position.

A step in the inductance sensing of rotor position that is also practiced involves commutation state calculation. Specifically, in the system 30 of this invention, motor processor 224 does more than base commutation state on a calibrated and normalized measure of motor phase inductance. Motor processor also reviews whether or not after one given commutation phase in inductance sensing is determined, the next determined phase is appropriate. Based on this determination, motor processor then places the motor 36 in the next appropriate commutation state. This process can be understood by reference to the flow chart of FIG. 29. Step 350, represents the transition from one peak sensed inductive current phase to a second peak sensed inductive current phase. After this transition occurs, in step 352, motor processor 224 determines whether or not the second peak sensed inductive current phase is one that is immediately adjacent the previously determined first peak sensed inductive current phase. By way of example to the calibrated and normalized peak currents of FIG. 28, if the immediate past current phase was the M3 Negative phase, than the immediately adjacent phases are the M2 Positive and M1 Positive phases. In step 352 if the sensed phase is from one of these two phases, it is assumed that motor is working properly. Then, in step 354, motor processor 224 instructs the appropriate FPGA 228 to make the next appropriate commutation shift of the energization signals applied to the windings.

However, in step 352 it may be determined, for example, that immediately after the M3 Negative sensed inductive current phase is highest, the next sensed highest inductive current is from the M3 Positive phase. This is because due to manufacturing tolerances, during the transition between the from M3 Negative and the M1 Positive phases being highest, the inductive sensed current corresponding to the M3 Positive phase is highest.

In response to this determination, in step 356, motor processor 224 determines whether or not the peak inductive sensed current for this new phase is reaches a level that is significantly higher than level for at which the phase transition between sensed currents occurs. In present example, motor processor 224 would only switch from motor driving based on the M3 Negative sensed phase to driving based on the rotor being in the M3 Positive phase, if the normalized inductive sensed current for the M3 Positive phase exceeds that of the last measured M3 Negative phase by a value of 0.5.

If, in step 356, it is determined that the apparently out of sequence inductance measurement is appreciably higher than the preceeding measurement, the measurement is accepted as accurate. Step 354 is executed. In this version of step 354, motor processor 224 instructs the appropriate FPGA 228 to make the next appropriate commutation shift of the energization signals based on the motor being in the detected phase.

Alternatively, in step 356 it may be determined that the apparently out of sequence inductive measurement is below this threshold value. If this determination is made, this highest determined inductive sensed phase is ignored. Instead, step 350 is reexecuted. In this, and in all executions of steps 350 and 352, inductance sensing monitor module 396 basis its determination on whether or not there has been a change in motor phase when the next expected phase is only marginally higher than the present phase. In the present example, the calibrated and normalized inductance sensed signal for the expected M1 Positive stage only has to be 0.1 higher than that of the present phase, the M3 Negative phase, for the motor processor 224 to determine that the motor rotor is now in a position corresponding to the M1 Positive phase.

In step 356 it may be determined that the out-of-sequence inductance sensed measurement is appreciably higher than the value of the inductance sensed measurement of the last phase. This "last phase inducatance sensed value" is from the crossing of the two inductance sensed signals. If this event occurs, it is interpreted by motor processor 224 as meaning that the motor rotor is actually in the position indicated by this new highest inductance sensed measurement. In this event, motor processor applies energization signals to the motor windings based on this new determination of rotor position.

An advantage of this feature of system 30 of this invention is that it essentially eliminates the likelihood that small out-of-sequence determinations of next highest motor phase that occur because of operation glitches and motor winding variations do not cause the motor controller 86 to incorrectly energize the windings based on erroneous determinations of rotor position.

Figure 30:
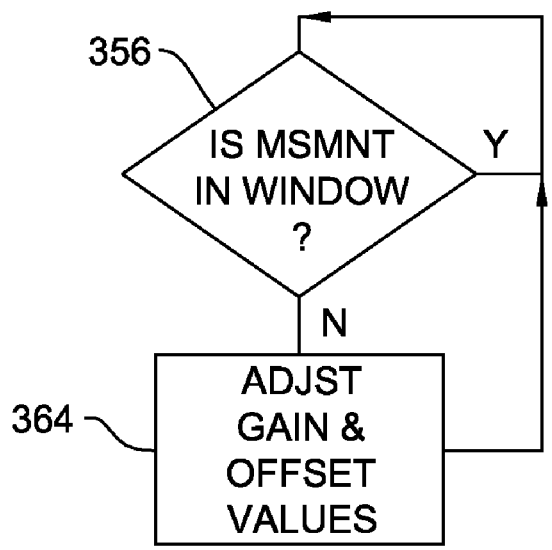
FIG. 30 is a flow chart of the process steps executed by the motor controller to during the inductance sensing mode to determine whether or not the gain and offset calibration values for a particular motor phase should be recalibrated.

Motor processor 224 of this invention further configured to adjust the gain and offset constants for the motor phases. Specifically as indicated by the flow chart of FIG. 30, in step 362 motor processor 224 determines, for each motor phase, whether or not, for a rotation of the rotor, the calibrated and normalized inductance sensed measurements are within a predefined window. This window can, for example be between −0.1 and 1.1. If in step 362 it is determined that the calibrated and sensed inductance sensed measurements for the phase are in this range, no recalibration is performed.

However, in step 362 it may be determined that the calibrated and normalized inductance sensed measurement is outside of the defined window. If this state is detected, in step 364, motor processor 224 performs adjustments of the gain and offset coefficients. These adjustments are performed iteratively until, in a subsequent execution of step 362 it is determined that the calibrated and normalized inductance sensed measurements for the motor phase are within the defined window.

This feature of the invention ensures that shifts of the inductance waveforms over time due to changes in temperature and component wear do not result in incorrect motor states from being calculated.

Still other methods of performing this recalibration is by locking the motor rotor in set of known positions and then taking inductance measurements. Recalibration is then made based on the measured inductance. Long term averages of sensed inductance measurements can also be employed to determine how to appropriate adjust the gain and offset values.

In some versions of the invention, display controller 64, through the NOVRAM interface 78 writes the recalculated gain and offset values from the motor phases into the handpiece EEPROM. These data are then read by the display calculator and used the next time the handpiece 34 is plugged into the control console.

In practice, this on the fly recalibration of the motor pole gain and offset values may be performed as soon as the inductance sensing process is initialized. The maximum and minimum normalized sensed inductance values are captured. If through a rotation of the motor rotor it is determined the peak-to-peak normalized sensed values exceed a value of 1.0 or are less than 1.0, the gain and offset values are recalculated by the motor processor 224 for this current run of the handpiece 34.

Many handpiece motors are constructed so that when rotor position based control switches from the inductance sensing mode to the BEMF sensing mode that energization sequence for the windings remains constant. Some motors 36 are, however, constructed so that when control shifts from between the inductance sensing and BEMF sensing modes, the energization sequence of the windings is reversed. Handpiece NOVRAM 72 thus contains a data flag, represented by BEMF/IS Reverse Energization Sequence field 368 in FIG. 27. The setting of this flag in field 368 indicates whether or not motor controller 86 upon switching between BEMF sensing and inductance sensing of rotor position should reverse the energization sequence of the windings.

Based on the setting of the flag in field 368, motor processor 224, upon changing sensing modes selectively also reverses the sequence in which the windings are commutated.

The above means of inductance sensing monitoring of motor rotor position is used to control the operation of the handpiece so the handpiece can provide the maximum amount of torque. In an alternative method of inductance sensing of rotor position, control console 32 is able to also provide precision speed regulation of the handpiece motor to 0 RPM.

Figure 31:
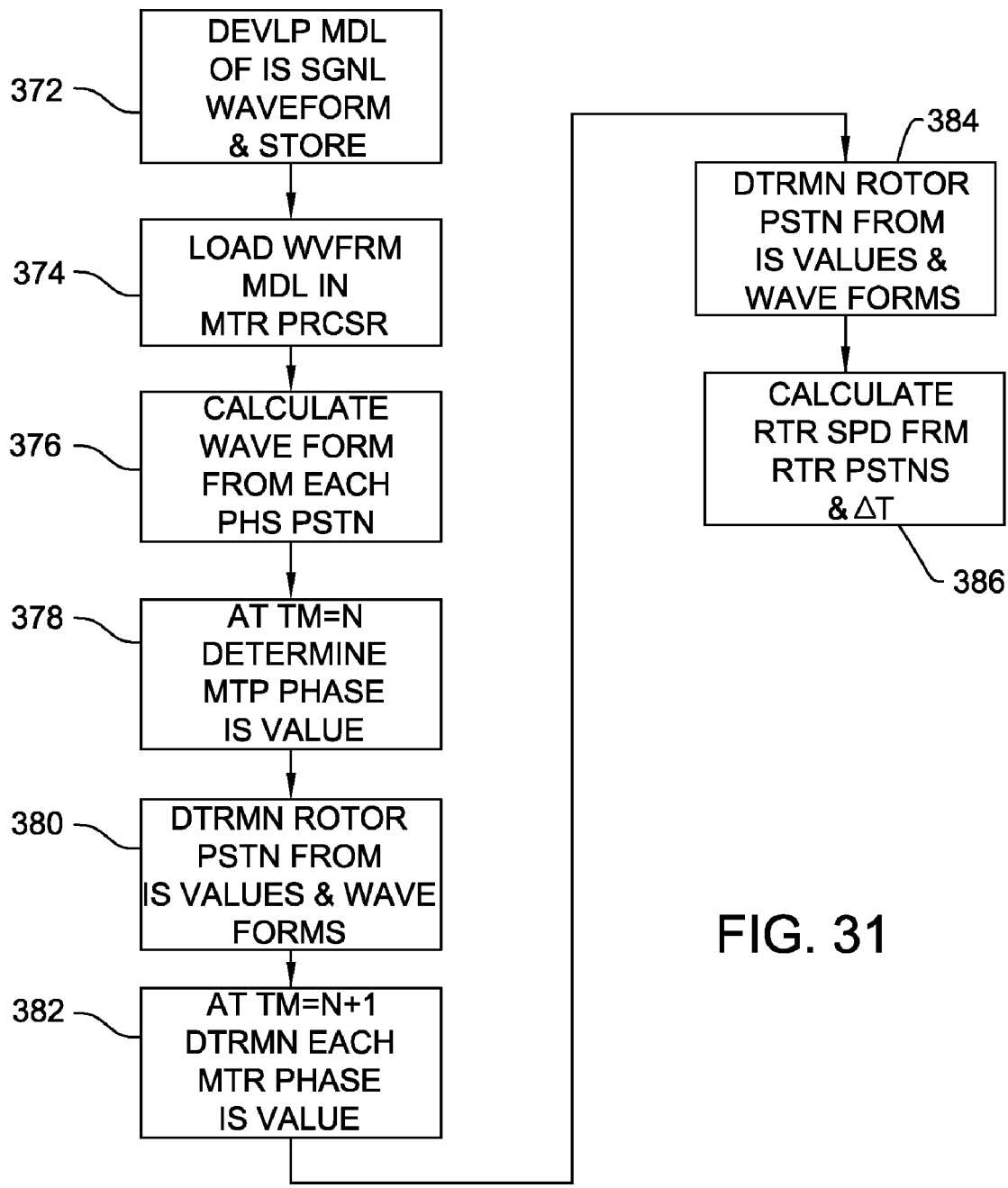
FIG. 31 is a flow chart of the process steps employed during handpiece manufacture and during operation of the system to user inter-commutation position calculations to, in inductance sensing mode, determine motor rotor position.

Specifically, in alternative version of this invention, a mathematical model of the inductance sense signal profile for a single motor pole is developed, step 372 in FIG. 31. A Fast Fourier Transformation can be used to create this model. (It is understood that not all inductance sensed signals have the sine wave profile of motor poles depicted in FIG. 28. The coefficients describing this signal profile are stored in the handpiece NOVRAM, field 370 in FIG. 27. These data are provided to the motor processor 224 in the initialization packet, step 374.

Upon receipt of the data, the motor processor 224 uses the data describing the single signal profile to develop a table indicating for every degree of rotor position, the excepted inductance sensed signal for each of the motor phases, step 376. When the handpiece motor is in the inductance sensed mode, the calibrated and normalized inductance sensed signal values for each of the six motor phases are determined from the measured data, step 378. These six calculated values are then matched to the closest set of table values, step 380. Thus, the matching of step 380 serves to determine, based on the plural inductance sensed calibrated and normalized values, the angular position of the motor rotor.

Steps 382 and 384 are repeats of steps 378 and 380, respectively, at a later time. Based on the difference in determined rotor position from steps 380 and 384 divided by the time difference, motor processor 224 is the able in step 386 to determine rotor speed.

The above method of inductance sensed speed is employed at low speeds where the BEMF signals typically are not strong enough to facilitate precision speed control. Generally, low speed for this type of control is consider a speed of 15% or lower of maximum motor speed, and more often a speed of 10% or lower of maximum motor speed.

The method, inductance sensing for inter-commutation rotor position determination, can be used to determine rotor position for speeds down to 0 RPM.

The means by which system 10 of this invention monitors the BEMF signals is now explained by reference to FIGS. 34A and 34B. Line segment 440 of the plot of FIG. 34 illustrates the theoretical rise in the BEMF signal across the unenergized winding 234. Arbitrarily, line segment 440 can be considered-the monitored BEMF signal across a first winding, the B1_SNS signal. Line segment 442 can be considered the monitored BEMF pulse across a second winding, the B2_SNS signal. Line segment 446 can be considered the monitored BEMF pulse across a third winding, the B3_SNS signal. The pattern then repeats.

In actuality, the changes in the switching of the commutation phases of the windings, a glitch is often present in the initial phase of a BEMF signal because of flyback currents. This is represented in by the down voltage glitch pulse 448 associated with line segment 442.

In order to avoid false determinations of rotor position based on these glitches, the FPGA BEMF monitor module 394 integrates the measured BEMF signals over time. More particularly, module 394 only integrates a particular BEMF signal starting from the time at which the signal is one-half through its rise or fall. Thus, with regard to the signal represented by line segment 440, BEMF monitoring module 394 only integrated the signal from the time represented by point 450. The BEMF signal represented by line segment 442 is only integrated from the time represented by point 452. The BEMF signal represented by line segment 444 is only integrated from the time represented by point 454.

The integrations of these BEMF signals are represented by the area under the integration curves in FIG. 34B. The BEMF monitor module 394 integrates each BEMF signal until a defined common threshold value is reached. This threshold value comes from the NOVRAM 72 in the initialization packet. This threshold value is represented by point 458 in FIG. 34B.

The time of the initial half way point for the initial BEMF signal, point 450 in FIG. 34A, comes from the commutation logic module 392. Module 392 also provides data upon which the time of second and third half way point, points 452 and 454, respectively, can be determined.

BEMF monitor module predicts when the next half way point, point 456 in FIG. 34A, according to the following process. Initially, module 394 determines when the peak integration value associated with the BEMF signal of line 440 occurs, point 458 on FIG. 34B. Then, the time at which the threshold value associated with the BEMF signal of line 442 occurs, point 460. The time between these two events is the actual time the BEMF signal of line 442 was at its true half way point. (For any given half-way time point of the BEMF signal, the difference between the predicted time and actual time is nominal.)

BEMF monitor module 394 determines the time at which the integration threshold value associated with the BEMF signal of line 446 is reached, point 462. Based on the time difference between the threshold values of points 460 and 462 occurred, module 394 determines the actual time, the BEMF signal of line 446 reached its half-way point. At this time BEMF monitor module 394 has in its memory data indicating when the signal of half way point 454 should have occurred and the time difference between when the half-way points of the transits of the BEMF signals of lines 442 and 446. BEMF monitor module 394 adds this time difference to the time at which the half-way transit represented by point 454 occurred. This sum is the prediction of when the BEMF signal represented by line 455 will occur, point 456. The BEMF monitoring module 394 thus starts it integration at this time.

In other versions of the invention, BEMF monitor module 394 may start integration before or after the half-way point of the BEMF signal transit. Generally though, switch glitches are over before this half-way point.

The half-way transit times of the transits of the later BEMF signals are repeatedly calculated in this manner. Thus, when the slope of the BEMF signals change as a result of speed changes of the handpiece motor 36, the predicted times of the half-way points of the signal's transits will similarly change. Thus, the half-way transit times predicted by the BEMF monitoring module, the times at which the module starts its integration process will, even with speed changes, closely approximate the true times.

It should be appreciated that the reason the signal is BEMF signal is integrated, as opposed to the monitoring of the occurrence of a 0 crossing, is to eliminate false determinations of motor phase due to high frequency noise.

Figure 35A:
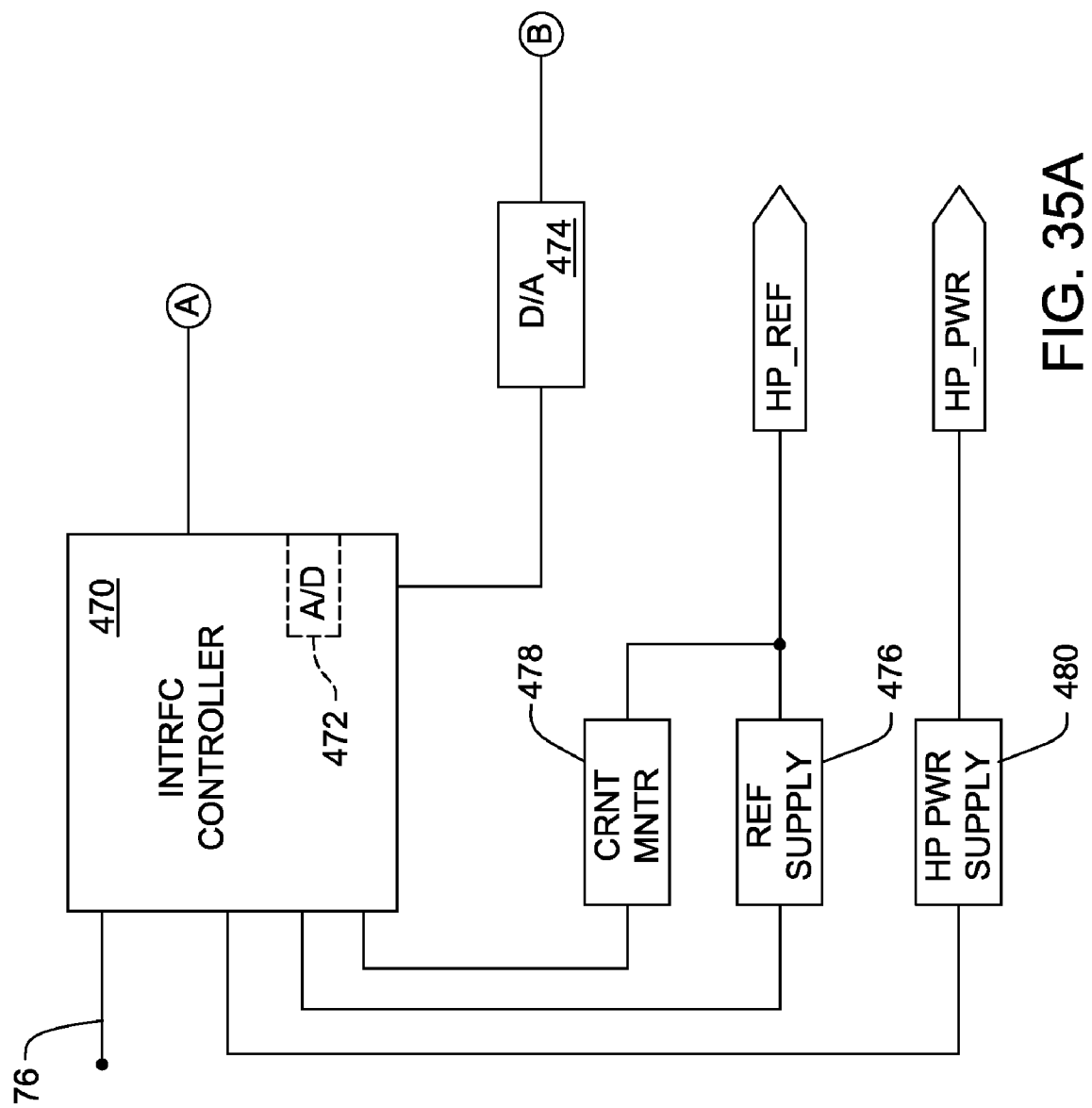
FIGS. 35A and 35B, when assembled together form a block and partial schematic diagram of the handpiece interface.
Figure 35B:
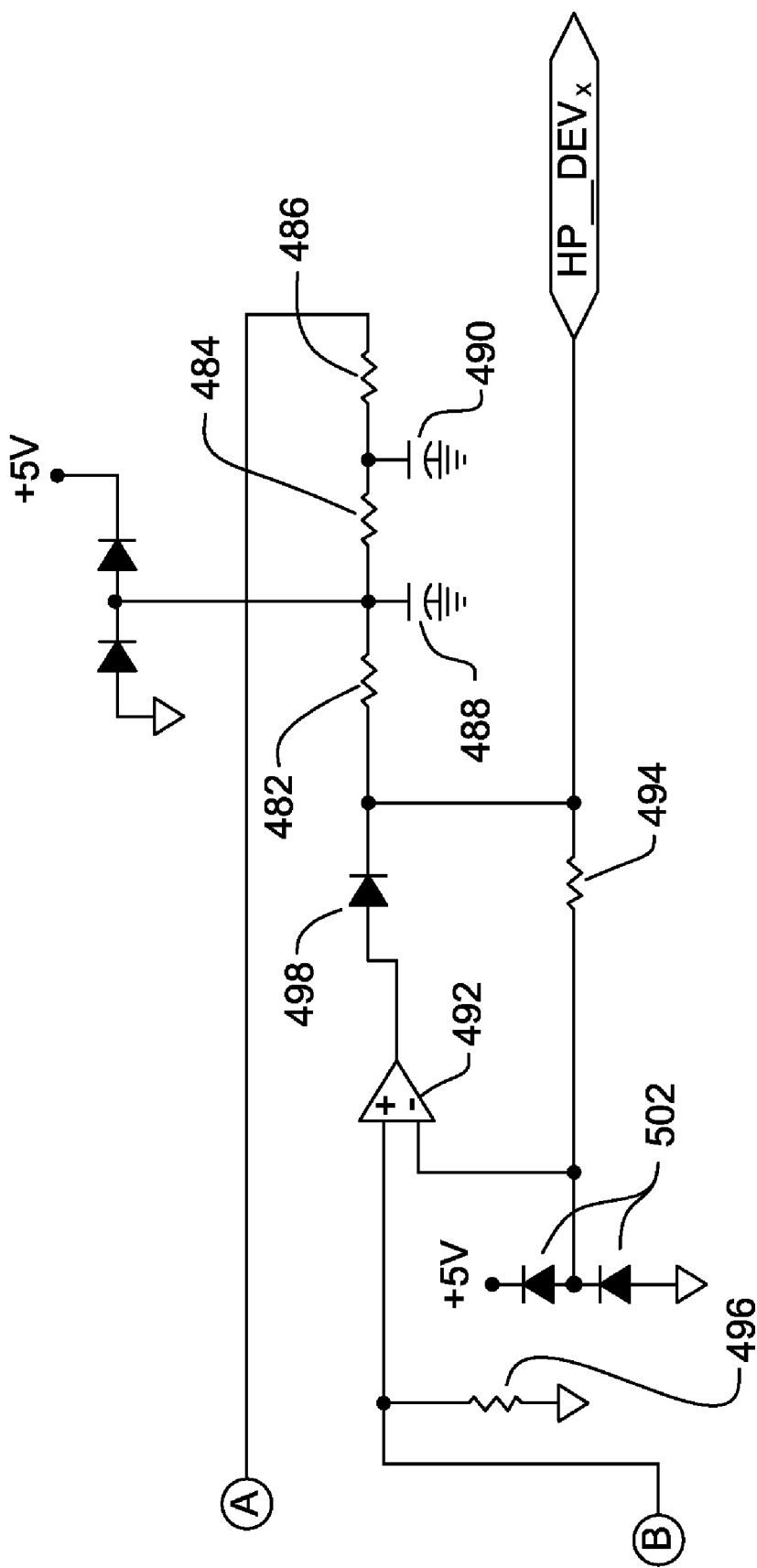

FIGS. 35A and 35B collectively illustrate the structure of a handpiece interface 70 of this invention. Interface 70 is able to connect to four devices integral with a handpiece 34 to which the interface is connected. For drawing simplicity, the connection circuit to only a single device, labeled the HP DEVX connection is shown. Interface 70 is able to transmit and receive both analog and digital signals to each handpiece device to which it is connected.

Handpiece interface 70 includes an interface controller 470. One suitable interface controller 470 can be constructed from the ATmega8 microcontroller. Controller 470 has an internal analog to digital circuit 472 for digitizing analog signals received from the connected handpiece devices. Controller 470 serves as the interface between the connected handpiece 34 and the display controller over bus 76. Analog signals interface controller 470 outputs to any handpiece device are output in digital form to a digital to analog converter 474. One suitable converter 474 is available from the Texas Instruments Corporation.

Interface 70 has a precision voltage supply 476. Voltage supply 476 outputs a precising 5 VDC voltage to the handpiece 34, the HP_REF signal. This voltage is then available to any components internal to the handpiece that may require a precision voltage. A current monitoring circuit 478 monitors the current of the HP_REF signal. If this current exceeds a certain level, it is assumed that there is a fault internal to the handpiece. If this current level is detected, monitoring circuit 478 forwards a fault signal to interface controller 470. Interface controller 470, in turn, sends an appropriate fault message to display controller 64.

Upon receipt of the fault message, display controller 64 presents an appropriate warning on display 42. Display controller 64 also inhibits the actuation of the handpiece 34 based on any signals generated by the handpiece sensors, the on handpiece controls. This is because the high current HP_REF signal is assumed to indicate there is malfunction with these controls.

Handpiece interface 70 also includes a handpiece power supply 480. Power supply 480 provides a power signal to the handpiece, the HP_PWR signal. This signal is available to any device internal to the handpiece other than motor 36 that may need power. Such a device may be a transmitting unit that is part of surgical navigation system.

Analog signals from the handpiece device through the HP_DEVx connection travel from the connection through an RC filter that includes three series connected resistors 482, 484 and 486. This filter also includes a capacitors 488 and 490. Capacitor 488 is tied between the junction of resistors 482 and 484 and ground. Capacitor 490 is tied between the junctions of resistors 484 and 486 and ground.

It is observed from FIG. 35B that the HP_DEVX connection is also attached to the inverting input of a buffer amplifier 492 through a resistor 494. The non-inverting input of buffer amplifier is connected to digital to analog converter 474. When the handpiece NOVRAM 72 data indicates analog signals are to be received from the connected device, based on instructions received from display controller 64, interface controller 470 configures the circuit. Specifically interface controller 470 causes digital to analog converter 474 to assert a signal to the non-inverting input of amplifier 492 that disables the amplifer. Since the amplifier is out of the circuit, signal flow is solely from the HP_DEVx connection to the RC filter.

The signal from the RC filter, the signal out of resistor 486 is applied to the controller analog to digital converter 472 for processing by the controller 470

In the event interface 70 is to output an analog signal to a handpiece device, controller 470 activates buffer amplifier 492. A digitized version of the signal is output from controller 470 to digital to analog converter 474. The analog signal produced by converter 474 is applied to the non-inverting input of buffer amplifier 492. Note a pull down resistor 496 is also tied between the non-inverting input to amplifier 492 and ground.

The analog signal out of amplifier 492 is applied through a diode 498 to the HP_DEVx connection.

Digital signals into interface 70 take the same conductive path from the HP_DEVX connection to controller 470 as the analog input signals. When digital signals are received, controller 470 disables its analog to digital converter 472. Consequently, the input signals are processed as digital signals.

Digital signals transmitted by the interface are transmitted by controller 470 through the controller terminal through which analog signals are normally received. The digital output signals thus pass through resistors 486, 484 and 482 to the HP_DEVX connection.

In FIG. 34B two zenner diodes 500 are shown reverse bias connected between the 5 VDC bus and ground. The junction between diodes 500 is connected to the junction between resistors 482 and 484. Two diodes 502 are similarly series connected and reverse biased between the 5 VDC bus and ground. Diodes 502 are connected at their common junction to the inverting input of buffer amplifier 492. Diodes 500 and 502 thus provide voltage protection for the interface.

In some versions of the invention a relay may be connected between the HP-DEVx connection and the interface circuit. This relay, when actuated, attaches the relay to the RFID interface 78. Thus, this relay is actuated to connect the HP_DEVx connection to the RFID interface 78 when the handpiece component is antenna designed to inductively exchange signals with a RFID associated with the handpiece.

It should be recognized that another feature of system 30 of this invention is that the display controller 64, motor controller 224 and the FPGAs 228 are totally reprogramable. For example, by entering instructions through the 1394 Interface 68, the algorithms of the PID modules 406 and 414 can be significantly modified. Thus, one or more of the motor drive and sense circuits 210 can be reset to operate in a direct drive mode or provide open loop control. Similarly, one or more the motor drive and sense circuits 210 can be reprogrammed to supply the energization signals to a handpiece 34 with a power consuming component that does not include a motor. Such handpieces include RF ablation tools, light emitting devices, electracautery devices and devices that drive ultrasonic tissue forming accessories.

It should therefore be appreciated that the above description is directed to one particular version of this invention. Other versions of the invention may have features different than what has been described. For example, each of the above features may not be incorporated into all versions of this invention.

Also, other versions of this invention may have different features. Other means than inductance sensing may be employed to provide the torque-down-to-stall control of the handpiece motor. Such means may, for example, involve open loop driving of the motor.

Other means may be employed to improve the way BEMF signals are used to determine rotor position for the purpose of regulating commutation.

What is claimed is:

1. A surgical handpiece control console, said control console including:

a plurality of connectors, each said connector configured to releaseably receive a separate surgical handpiece having an electrical power consuming unit so that plural surgical handpieces can be simultaneously connected to said control console;

a plurality of drivers, each said driver configured to, in response to an instruction signal specifically generated for that said driver, supply an energization signal to one of the surgical handpiece power consuming units through said connector that receives the handpiece, wherein said drivers are collectively configured to simultaneously supply energization signals to separate ones of the plural surgical handpiece power consuming units and the plurality of said drivers is less than the plurality of said connectors;

a switch assembly connected between said drivers and said connectors so that the energization signal output by any one of said drivers can be output through any one of said connectors to the handpiece connected to said connector; and a control processor connected to said drivers and said switch assembly that: receives command signals including command signals generated by plural input devices that are external from said control console; evaluate the received command signals; if the evaluation indicates that the received command signal is a command signal to actuate a first one of the surgical handpieces, generates an instruction signal to one of said drivers that causes the said driver to supply a specific energization signal for the first surgical handpiece power consuming unit based on the command signal and sets said switch assembly so that the energization signal output by the said driver is output through said connector to which the first handpiece is connected; and, if the evaluation indicates that the received command signal is a command signal to actuate a second one of the surgical handpieces, generates an instruction signal to another one of said drivers that causes the other said driver to supply a specific energization signal for the second surgical handpiece power consuming unit based on the command signal and sets said switch assembly so that the energization signal output by the other said driver is output through said connector to which the second handpiece is connected wherein the energization signals from both said drivers are simultaneously output through said switch assembly.

2. The surgical handpiece control console of claim 1, further including:

a power supply for sourcing the power that forms the energization signals supplied by said drivers; and a power supply monitor connected to said power supply for determining if the power sourced by said power supply exceeds a threshold level; and wherein, said control processor is further configured to, when said power supply monitor determines the power sourced by said power supply exceeds the threshold level, generate instructions to limit the outputting of energization signals by one of said drivers.

3. The surgical handpiece control console of claim 1, wherein:

each said driver is custom configurable so that the said driver outputs an energization signal based on the received instruction signal and the custom configuration of said driver; and said control processor is further configured to:
read data from memories associated with the surgical handpieces;
for a handpiece, based on the data read from the handpiece memory, custom configure the said driver that supplies energization signals to the handpiece.

4. The surgical handpiece control console of claim 1, wherein:

each said driver receives a feedback signal from the surgical handpiece to which said driver supplies energization signals; filters the feedback signal to produce a filtered feedback signal; and, based on the filtered feedback signal, selectively supplies energization signals to the surgical handpiece wherein, the filtering is performed by an adjustable filter; and said control processor is further configured to:
read data from memories integral with the surgical handpieces; and
based on the data read from the surgical handpiece memory of the handpiece associated with a said driver, adjust the said filter of the said driver that supplies energization signals to the handpiece.

5. The surgical handpiece control console of claim 1, wherein:

each said driver supplies energization signals to the associated surgical handpiece based on a control algorithm, the control algorithm having variable coefficients; and said control processor is further configured to:
read data from memories integral with the surgical handpieces; and
based on the data read from the surgical handpiece memory of the handpiece associated with a said driver, set the coefficients of the control algorithm of the said driver that supplies energization signals to the handpiece.

6. The surgical handpiece control console of claim 1, further including:

a display connected to said control processor;

a user interface associated with said display, said user interface configured to transmit control signals to said control processor;

wherein, said control processor is further configured to:
determine for a control signal received over said user interface, the handpiece for which the control signal is intended and the type of control signal;
present on the said display: plural images on said display, including images identifying the types of the handpieces connected to said console and, based on control signals entered over said user interface, images indicating the type of control signal and the handpiece for which the control signal is entered; and
for the received control signal, configure the said driver that applies energization signals to the handpiece with which the control signal is associated so that the energization signals are supplied to the surgical handpieces based on the received control signal.

* * * * *